United States Patent
Behabtu et al.

(10) Patent No.: US 10,392,641 B2
(45) Date of Patent: *Aug. 27, 2019

(54) ENZYMATICALLY PRODUCED CELLULOSE

(71) Applicant: E I DU PONT DE NEMOURS AND COMPANY, Wilmington, DE (US)

(72) Inventors: Natnael Behabtu, Wilmington, DE (US); Aryookaran J. Poulose, Belmont, CA (US); Zheyong Yu, Shanghai (CN); Zhenghong Zhang, Shanghai (CN)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/191,483

(22) Filed: Nov. 15, 2018

(65) Prior Publication Data
US 2019/0100782 A1 Apr. 4, 2019

Related U.S. Application Data

(62) Division of application No. 15/532,550, filed as application No. PCT/US2015/065707 on Dec. 15, 2015, now Pat. No. 10,131,929.

(30) Foreign Application Priority Data

Dec. 23, 2014 (WO) ................ PCT/CN2014/094593
Dec. 23, 2014 (WO) ................ PCT/CN2014/094594

(51) Int. Cl.
*C12N 9/10* (2006.01)
*C08L 1/02* (2006.01)
*C12P 19/04* (2006.01)
*C12P 19/18* (2006.01)
*C09D 101/02* (2006.01)

(52) U.S. Cl.
CPC ................ *C12P 19/18* (2013.01); *C08L 1/02* (2013.01); *C09D 101/02* (2013.01); *C12N 9/1051* (2013.01); *C12P 19/04* (2013.01); *C12Y 204/01049* (2013.01)

(58) Field of Classification Search
None
See application file for complete search history.

(56) References Cited

U.S. PATENT DOCUMENTS

| | | | |
|---|---|---|---|
| 4,435,307 | A | 3/1984 | Barbesgaard et al. |
| 5,352,602 | A | 10/1994 | Yamado et al. |
| 5,716,837 | A | 2/1998 | Barry et al. |
| 5,776,757 | A | 7/1998 | Schuelein et al. |

(Continued)

OTHER PUBLICATIONS

International Search Report and Written Opinion, PCT International Application PCT/US2015/065707, dated Feb. 17, 2016.

(Continued)

*Primary Examiner* — Richard C Ekstrom

(57) ABSTRACT

Enzymatic reactions are disclosed herein comprising water, glucose-1-phosphate, cellodextrin, and at least one cellodextrin phosphorylase enzyme comprising an amino acid sequence that is at least 90% identical to SEQ ID NO:2 or SEQ ID NO:6. These reactions produce a low molecular weight, insoluble cellulose with enhanced features.

14 Claims, 4 Drawing Sheets

Figure 1A:
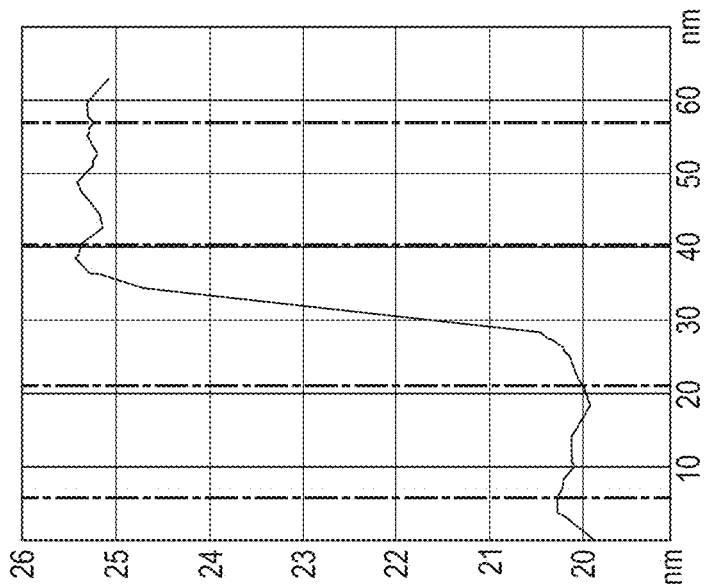
Figure 1A:
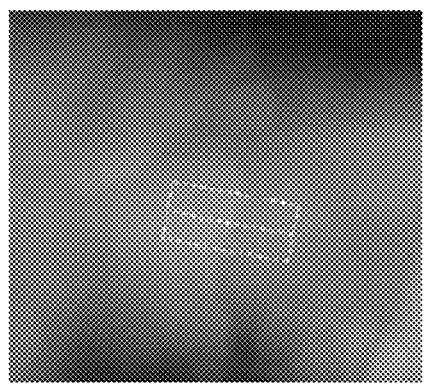
Figure 1A:
Figure 1A:
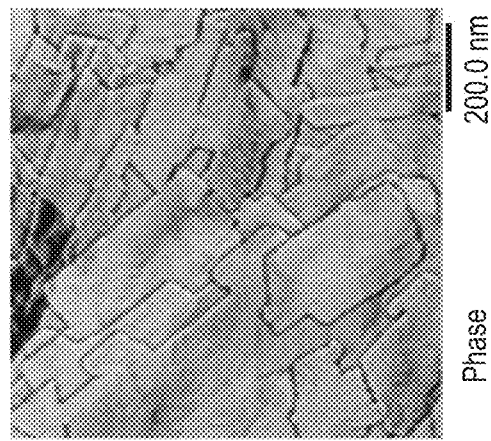

Specification includes a Sequence Listing.

(56) References Cited

U.S. PATENT DOCUMENTS

| | | | |
|---|---|---|---|
| 5,811,277 | A | 9/1998 | Fang et al. |
| 7,229,801 | B2 | 6/2007 | Fujii |
| 7,399,623 | B2 | 7/2008 | Miller et al. |
| 7,449,320 | B2 | 11/2008 | Miller et al. |
| 7,604,974 | B2 | 10/2009 | Jones et al. |
| 7,615,365 | B2 | 11/2009 | Caimi et al. |
| 7,906,306 | B2 | 3/2011 | Svendsen |
| 7,968,309 | B2 | 6/2011 | Fujii et al. |
| 8,354,101 | B2 | 1/2013 | England et al. |
| 8,735,105 | B2 | 5/2014 | Hoff et al. |
| 8,889,379 | B2 | 11/2014 | Tran et al. |
| 10,131,929 | B2 * | 11/2018 | Behabtu ............... C12P 19/04 |
| 2002/0133849 | A1 | 9/2002 | Kossmann et al. |
| 2013/0059340 | A1 | 3/2013 | Tran et al. |
| 2014/0057323 | A1 | 2/2014 | Doudna et al. |
| 2014/0087435 | A1 | 3/2014 | Chen et al. |
| 2017/0327857 | A1 * | 11/2017 | Behabtu ............... C12P 19/04 |
| 2018/0216086 | A1 * | 8/2018 | Koch ............... C12P 19/02 |
| 2018/0334696 | A1 * | 11/2018 | Behabtu ............... C12P 19/04 |

OTHER PUBLICATIONS

Genbank Accession No. WP_015559149.1, Chitobiose Phosphorylase [Ruminococcus Champanellensis] May 19, 2013, pp. 1-2.

Genbank Accession No. WP_051680808.1, Glycosyl Transferase [Vibrio Rhizosphaerae], Aug. 16, 2015, p. 1.

Genbank Accession No. WP_027594019.1, Glycosyl Transferase [Vibrio Gazogenes], Jun. 12, 2014, p. 1.

Chassard et al., *Ruminococcus champanellensis* sp. Nov., A Cellulose-Degrading Bacterium From Human Gut Microbiota, International Journal of Systematic and Evolutionary Microbiology, vol. 62 (2012), pp. 138-143.

Chawla et al., Microbial Cellulos: Fermentative Production and Applications, Food Technol. Biotechnol., vol. 47, No. 2 (2009), pp. 107-124.

Eibinger et al., Cellulose Surface Degradation by a Lytic Polysaccharide Monooxygenase and Its Effect on Cellulase Hydrolytic Efficiency, Journal of Biological Chemistry, vol. 289, No. 52 (2014), pp. 35929-35938.

Hattori et al., Enzymatic Synthesis of Cellulose II-Like Substance via Cellulolytic Enzyme-Mediated Transglycosylation in an Aqueous Medium, Carbohydrate Research, vol. 353 (2012), pp. 22-26.

Hiraishi et al., Synthesis of Highly Ordered Cellulose II In Vitro Using Cellodextrin Phosphorylase, Carbohydrate Research, vol. 344 (2009), pp. 2468-2473.

Iguchi et al., Review Bacterial Cellulose—A Masterpiece of Nature's Arts, Journal of Materials Science, vol. 35 (2000), pp. 261-270.

Isaksen et al.. A C4-Oxidating Lytic Polysaccharide Monooxygenase Cleaing Both Cellulose and Cello-Oligosaccharides, Journal of Biological Chemistry, vol. 289, No. 5 (2014), pp. 2632-2642.

Kadokawa et al., Synthesis of New Polysaccharide Materials by Phosphorylase-Catalyzed Chain-Elongation, Polymer Preprints, vol. 52, No. 1 (2011), pp. 59-60.

Klemm et al., 10 Cellulose (On-Line), Mar. 7, 2003 or Earlier, http://www.wileyvch.de/books/biopoly/pdf_v06/bpol6010_275_287. pdf, pp. 275-287.

Kobayashi et al., Novel Method for Polysaccharide Synthesis Using an Enzyme: The First In Vitro Synthesis of Cellulose via a Nonbiosynthetic Path Utilizing Cellulase as a Catalyst, J. Am. Chem. Soc., vol. 113 (1991), pp. 3079-3084.

Kolpak et al., Determination of the Structure of Cellulose II, Macromolecules, vol. 9, No. 2 (1976), pp. 273-278.

Kroon-Batenberg, The Crystal and Molecular Structures of Cellulose I and II, Glycoconjugate Journal, vol. 14, Issue 5 (1997), pp. 677-690.

Lou et al., Cellobiose and Cellodextrin Metabolism by the Ruminal Bacterium *Ruminococcus albus*, Current Microbology, vol. 35 (1997), pp. 221-227.

Maki et al., Prospects of Cellulase-Producing Bacteria for the Bioconversion of Lignocellulosic Biomass, Int. J. Biol. Sci, vol. 5, No. 5 (2009), pp. 500-516.

Nakai et al., Efficient Chemoenzymatic Oligosaccharide Synthesis by Reverse Phosphorolysis Using Cellobiose Phosphorylase and Cellodextrin Phosphorylase From Clostridium Thermocellum, Biochimie, vol. 92 (2010), pp. 1818-1826.

Petrovic et al., Characterization of Oligocellulose Synthesized by Reverse Phosphorolysis Using Different Cellodextrin Phosphorylases, Anal. Chem, vol. 87 (2015), pp. 9639-9646.

Pineda et al., Tecnicas De Fermentacion Y Aplicaciones De La Celulosa Bacteriana: Una Revision, Ingenieria Y Ciencia, vol. 8, No. 16 (2012), pp. 307-335 (English Abstract Only; No Translation for Remainder of Document).

Romling et al., Bacterial Cellulose Biosynthesis: Diversity of Operons, Subunits, Products and Functions, Trends in Microbiology, vol. 23, No. 9 (2015) pp. 545-557.

Ross et al., Cellulose Biosynthesis and Function in Bacteria, Microbiological Reviews, vol. 55, No. 1 (1991), pp. 35-58.

Sawano et al., Characterization of Ruminococcus Albus Cellodextrin Phosphorylase and Identification of a Key Phenylalanine Residue for Acceptor Specificity and Affinity to the Phosphate Group, The FEBS Journal, vol. 280 (2013), pp. 4463-4473.

Tiwari et al., Starch Phosphorylase: Biochemical and Biotechnoogical Perspectives, Biotechnology and Molecular Biology Review, vol. 7, No. 3 (2012), pp. 69-83.

Waldmann et al., Preliminary Communication—The Enzymic Utilization of Sucrose in the Synthesis of Amylose and Derivatives of Amylose, Using Phosphorylases, Carbohydrate Research, vol. 157 (1986), pp. C4-C7.

* cited by examiner

ENZYMATICALLY PRODUCED CELLULOSE

This application is a continuation of U.S. application Ser. No. 15/532,550 (filed Jun. 2, 2017, now U.S. Pat. No. 10,131,929), which is the National Stage application of International Application No. PCT/US2015/065707 (filed Dec. 15, 2015), which claims the benefit of International Application No. PCT/CN2014/094594 (filed Dec. 23, 2014), all of which prior applications are incorporated herein by reference in their entireties.

FIELD OF INVENTION

The present disclosure is in the field of polysaccharides. More specifically, the disclosure pertains to low molecular weight insoluble cellulose and enzymatic reactions for its synthesis. The disclosure also regards using cellulose in various applications such as viscosity modification and film production.

REFERENCE TO SEQUENCE LISTING SUBMITTED ELECTRONICALLY

The official copy of the sequence listing is submitted electronically via EFS-Web as an ASCII formatted sequence listing with a file named CL6392WOPCT2_ Sequence-Listing_ST25 created on Dec. 9, 2015 and having a size of 39.4 kilobytes and is filed concurrently with the specification. The sequence listing contained in this ASCII-formatted document is part of the specification and is herein incorporated by reference in its entirety.

BACKGROUND

Driven by a desire to find new structural polysaccharides using enzymatic syntheses or genetic engineering of microorganisms, researchers have discovered polysaccharides that are biodegradable and can be made economically from renewably sourced feedstocks. One such polysaccharide is cellulose, a glucan polymer characterized by having beta-1,4-glycosidic linkages.

Microcrystalline cellulose (MCC) is a white, odorless, tasteless, relatively free flowing, crystalline powder that is virtually free from organic and inorganic contaminants. It is a purified, partially depolymerized cellulose obtained by subjecting alpha cellulose obtained as a pulp from fibrous plant material (e.g., wood) to hydrolytic degradation, typically with mineral acid. MCC is a highly crystalline particulate cellulose consisting primarily of crystalline aggregates obtained by removing amorphous (fibrous cellulose) regions of a cellulosic material. MCC is used in a variety of applications including foods, pharmaceuticals and cosmetics. Despite MCC's various applications, preparation of this cellulose type is laborious and expensive. Also, activation of MCC requires high shear.

Development of new forms of cellulose is desirable given the potential utility thereof in various applications. The development of novel enzymatic processes may be a useful means for producing new types of cellulose material.

SUMMARY OF INVENTION

In one embodiment, the present disclosure concerns an enzymatic reaction comprising water, glucose-1-phosphate, cellodextrin, and a cellodextrin phosphorylase enzyme that synthesizes insoluble cellulose. In another embodiment, the cellodextrin phosphorylase enzyme comprises an amino acid sequence that is at least 90% identical to SEQ ID NO:2 or SEQ ID NO:6, and synthesizes insoluble cellulose.

In another embodiment, the weight-average degree of polymerization ($DP_w$) of the cellulose is (i) about 10 to about 30, or (ii) about 10 to about 1000.

In another embodiment, the cellodextrin comprises cellobiose.

In another embodiment, the present disclosure concerns a method for producing insoluble cellulose. This method comprises a) contacting at least water, glucose-1-phosphate, cellodextrin, and a cellodextrin phosphorylase enzyme such as one comprising an amino acid sequence that is at least 90% identical to SEQ ID NO:2 or SEQ ID NO:6, wherein insoluble cellulose is produced; and b) optionally isolating the insoluble cellulose produced in step (a).

In another embodiment, the cellulose produced in step (a) of the method has a weight-average degree of polymerization ($DP_w$) of (i) about 10 to about 30, or (ii) about 10 to about 1000. The cellulose produced in step (a) of the method has a cellulose II crystal structure in another embodiment.

In another embodiment, the cellodextrin employed in the method comprises cellobiose.

In another embodiment, glucose-1-phosphate is provided in step (a) of the method by providing a second reaction, wherein the products of the second reaction comprise glucose-1-phosphate. In another embodiment, the second reaction produces glucose-1-phosphate by (i) contacting water, inorganic phosphate, starch, a starch phosphorylase, and optionally a starch debranching enzyme such as a pullulanase or isoamylase; (ii) contacting water, inorganic phosphate, sucrose, and a sucrose phosphorylase enzyme; or (iii) contacting water, inorganic phosphate, cellulosic biomass, an endoglucanase, a cellodextrin phosphorylase, and optionally, a lytic polysaccharide monooxygenase and/or a cellobiohydrolase. In another embodiment, the second reaction is provided in the same vessel in which step (a) is performed, and the second reaction is performed before and/or continuously with step (a).

BRIEF DESCRIPTION OF THE DRAWINGS AND SEQUENCES

FIG. 1A: Atomic force microscopy (AFM) was used to analyze a thin film made from drying a colloidal dispersion of insoluble cellulose synthesized by an R. champanellensis cellodextrin phosphorylase enzyme. The thickness of the sheet structure is about 5 nm. Refer to Example 4.

Figure 1B:
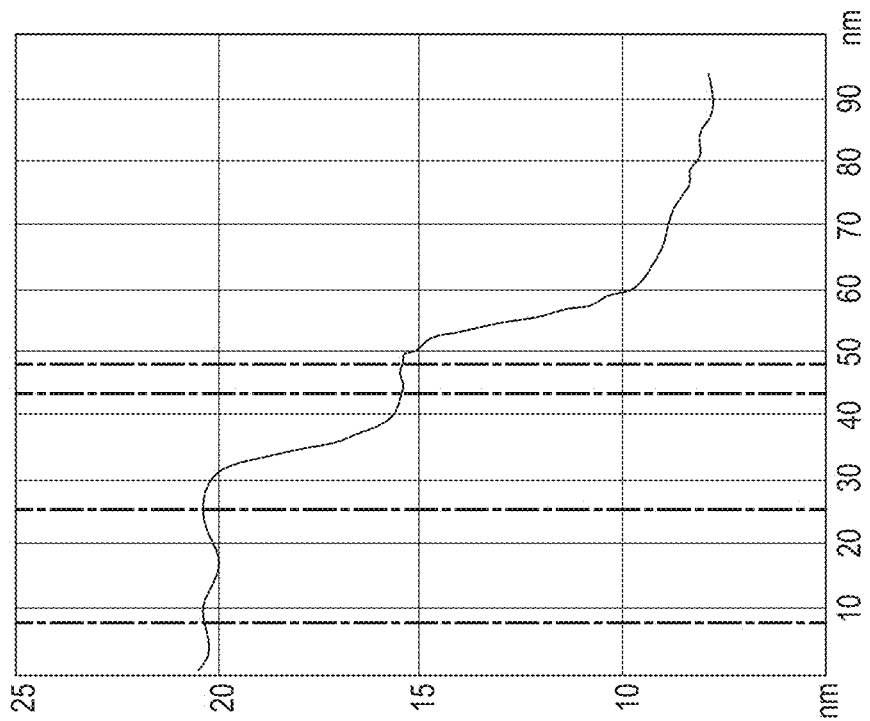
Figure 1B:
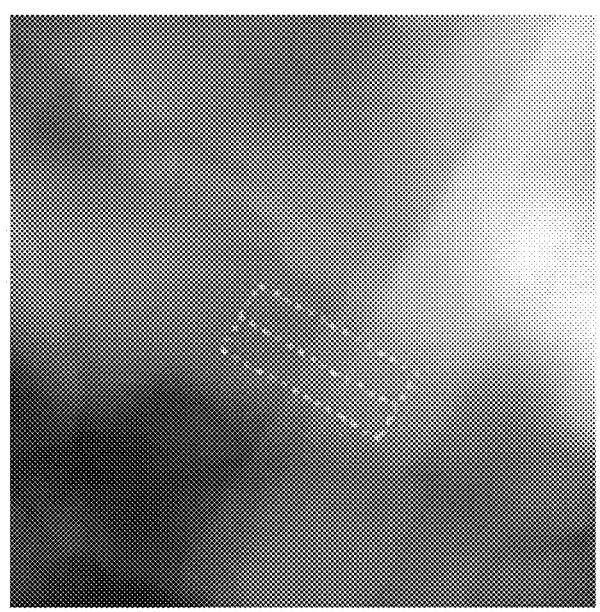

FIG. 1B: AFM was used to analyze a thin film made from drying a colloidal dispersion of insoluble cellulose synthesized by a V. ruber cellodextrin phosphorylase enzyme. The thickness of the sheet structure is about 4.8 nm. Refer to Example 4.

Figure 2:
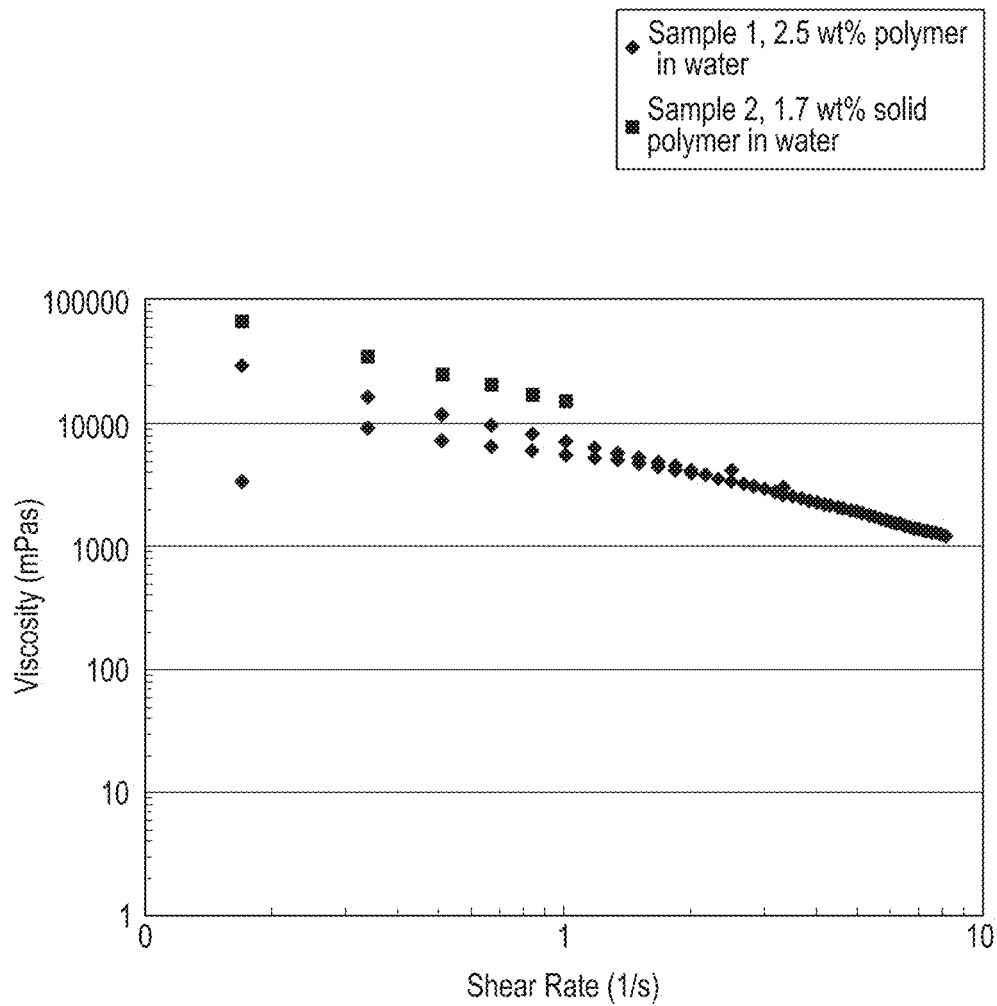

FIG. 2: Viscosity versus shear rate, as measured for colloidal dispersions of insoluble cellulose material synthesized by R. champanellensis cellodextrin phosphorylase (blue diamonds, sample 1, 2.5 wt % in water) or V. ruber cellodextrin phosphorylase (red squares, sample 2, 1.7 wt % in water). Refer to Example 4.

Figure 3:
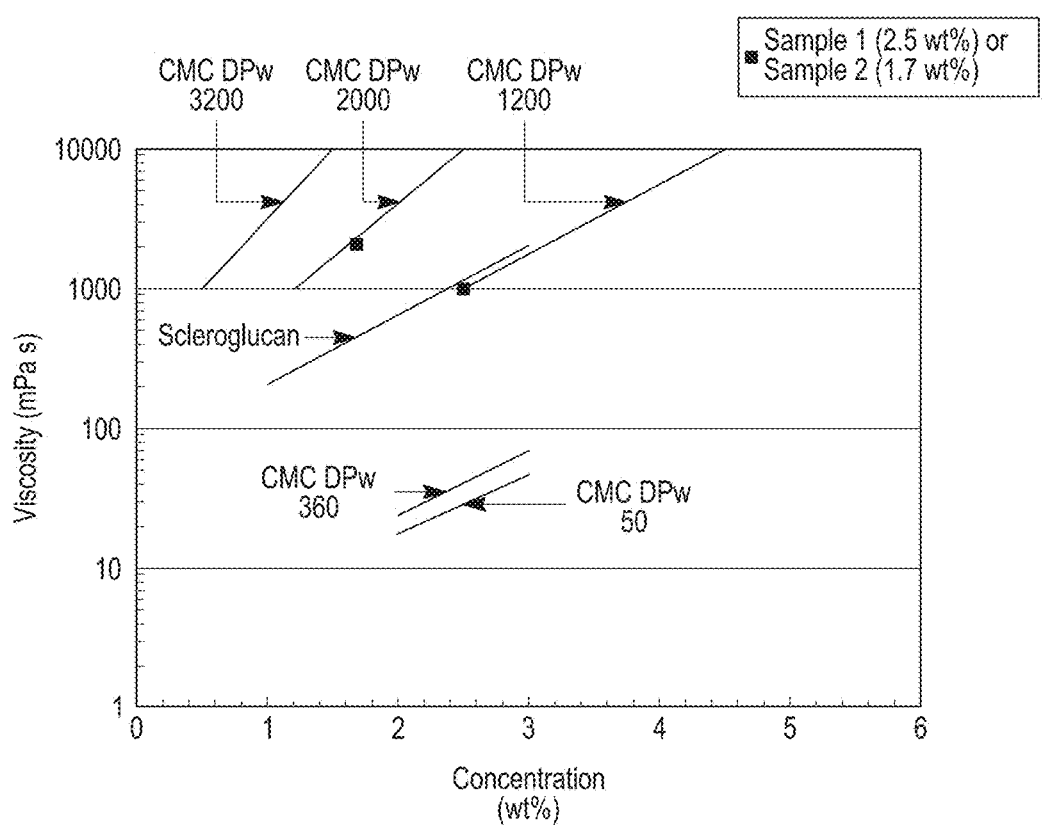

FIG. 3: Viscosity of various commercially available water-soluble polysaccharides (carboxymethyl cellulose [CMC] and scleroglucan) in water compared to the viscosity of colloidal dispersions of insoluble cellulose material synthesized by R. champanellensis cellodextrin phosphorylase (2.5 wt % in water) or V. ruber cellodextrin phosphorylase (1.7 wt % in water). CMC of $DP_w$ 3200 and 2000 were from CP Kelco, and CMC of $DP_w$ 50, 360 and 1200 were FINNFIX brand CMC from CP Kelco. Scleroglucan was from Cargill (ACTIGUM). Viscosity measurements are reported at 10 1/s shear rate.

TABLE 1

Summary of Nucleic Acid and Protein SEQ ID Numbers

| Description | Nucleic acid SEQ ID NO. | Protein SEQ ID NO. |
| --- | --- | --- |
| "VruCdp1", *Vibrio ruber* DSM14379 cellodextrin phosphorylase. | 1 (2415 bases) | 2 (805 aa) |
| "VruCdp1", *Vibrio ruber* DSM14379 cellodextrin phosphorylase. Nucleotide sequence codon-optimized for expression in *E. coli*. Amino acid sequence contains additional C-terminal residues (L-E-6xHis). | 3 (2442 bases) | 4 (813 aa) |
| "RchCdp1", *Ruminococcus champanellensis* 18P13 cellodextrin phosphorylase. GENBANK Accession No. WP_015559149 (amino acid sequence). | 5 (2397 bases) | 6 (798 aa) |
| "RchCdp1", *Ruminococcus champanellensis* 18P13 cellodextrin phosphorylase. Nucleotide sequence codon-optimized for expression in *E. coli*. Amino acid sequence contains additional C-terminal residues (L-E-6xHis). | 7 (2421 bases) | 8 (806 aa) |

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" is recited, the recited range should be construed as including ranges "1 to 4", "1 to 3", "1-2", "1-2 & 4-5", "1-3 & 5", and the like.

The terms "cellodextrin phosphorylase", "cellodextrin phosphorylase enzyme" and the like are used interchangeably herein. A cellodextrin phosphorylase is of the Enzyme Commission (EC) entry 2.4.1.49 and belongs to glycosyl hydrolase family 94 (GH94) according to the CAZy (Carbohydrate-Active EnZymes) database. A cellodextrin phosphorylase can reversibly catalyze synthesis of cellulose and free phosphate (products) from alpha-D-glucose-1-phosphate and cellodextrin (substrates). Such a reaction can also be written as: glucose-1-phosphate+(1,4-beta-D-glucosyl)$_{n-1}$→(1,4-beta-glucosyl)$_n$+phosphate, where "(1,4-beta-D-glucosyl)$_{n-1}$" refers to cellodextrin and "(1,4-beta-glucosyl)$_n$" refers to cellulose. A cellodextrin phosphorylase in certain aspects herein can synthesize low molecular weight cellulose (e.g., $DP_w$ of 10-30) that is insoluble in aqueous compositions. A cellodextrin phosphorylase in certain aspects herein comprises an amino acid sequence that is at least 90% identical to SEQ ID NO:2 or 6.

The term "cellulose" refers to a glucan polysaccharide having a linear chain of beta-1,4-linked D-glucose monomeric units. Cellulose can optionally be represented as (1,4-beta-D-glucosyl)$_n$, where n can be the same value as a $DP_w$ value of a low molecular weight cellulose as disclosed herein (e.g., 10 to 30). The term "glucan" herein refers to a polysaccharide of D-glucose monomers that are linked by glucosidic linkages, which are a type of glycosidic linkage.

The terms "cellulose II structure", "cellulose II crystal structure", "cellulose II" and the like are used interchangeably herein. Cellulose II structure has been described by Kolpak and Blackwell (*Macromolecules* 9:273-278) and Kroon-Batenburg and Kroon (*Glycoconjugate J.* 14:677-690), for example, both of which are incorporated herein by reference. The dominant hydrogen bonds characterizing cellulose II structure are O2-H—O6, O6-H—O6 and O2-H—O2, whereas cellulose I has O2-H—O6 as a dominant hydrogen bond. The structure of cellulose II comprises chain folding and is difficult to unravel. Cellulose II comprises anti-parallel chains, whereas in contrast, cellulose I chains are parallel.

The terms "glycosidic linkage", "glycosidic bond" and the like are used interchangeably herein and refer to the covalent bond that joins a carbohydrate molecule to another carbohydrate molecule. The terms "glucosidic linkage", "glucosidic bond" and the like are used interchangeably herein and refer to a glycosidic linkage between two glucose molecules in a glucan. The term "beta-1,4-glucosidic linkage" as used herein refers to the covalent bond that joins glucose molecules to each other through carbons 1 and 4 on adjacent glucose monomers in a glucan.

The glycosidic linkage profile of cellulose herein can be determined using any method known in the art. For example, a linkage profile can be determined using methods that use nuclear magnetic resonance (NMR) spectroscopy (e.g., $^{13}$C NMR or $^1$H NMR). These and other methods that can be used are disclosed in *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The "molecular weight" of a saccharide polymer herein, such as cellulose, can be represented as number-average molecular weight ($M_n$) or as weight-average molecular weight ($M_w$), the units of which are in Daltons or grams/mole. Alternatively, molecular weight can be represented as $DP_w$ (weight average degree of polymerization) or $DP_n$ (number average degree of polymerization). Various means are known in the art for calculating these molecular weight measurements such as with high-pressure liquid chromatography (HPLC), size exclusion chromatography (SEC), or gel permeation chromatography (GPC).

The term "cellodextrin" as used herein refers to one or more glucose polymers having a length of two or more beta-1,4-linked glucose monomers. Cellodextrin is typically produced via (enzymatic) hydrolysis of cellulose. "Cellobiose" is a type of cellodextrin that comprises two beta-1,4-linked glucose monomers (i.e., cellobiose is a type of disaccharide).

"Glucose-1-phosphate" (G1P) as used herein refers to a glucose molecule with a phosphate group on the 1-carbon. G1P herein can be alpha-D-glucose-1-phosphate.

The terms "enzymatic reaction", "cellodextrin phosphorylase reaction" and the like are used interchangeably herein and, except as otherwise noted, refer to a reaction that is performed by a cellodextrin phosphorylase enzyme. An enzymatic reaction generally refers to a solution comprising at least one active cellodextrin phosphorylase enzyme in a solution comprising water, glucose-1-phosphate, and cellodextrin (e.g., cellobiose), and optionally other components. It is in a cellodextrin phosphorylase reaction where the step of contacting water, glucose-1-phosphate, cellodextrin and a cellodextrin phosphorylase enzyme is performed. The term "under suitable reaction conditions" and the like refer to reaction conditions that support conversion of substrate to low molecular weight, insoluble cellulose via cellodextrin phosphorylase enzyme activity. A cellodextrin phosphorylase reaction herein is not naturally occurring. It would be understood that, as a cellodextrin phosphorylase reaction produces insoluble cellulose, such cellulose is present out of solution.

A "control" enzymatic reaction as used herein can refer to a reaction using a cellodextrin phosphorylase not comprising an amino acid sequence that is at least 90% identical to SEQ ID NO:2 or 6, for example. All the other features (e.g., substrate concentration, temperature, pH, time) of a control reaction solution can be the same as the reaction to which it is being compared.

A "second reaction" as used herein refers to a reaction that is in addition to a cellodextrin phosphorylase reaction ("first reaction"), and which provides G1P substrate for the first reaction.

"Inorganic phosphate", which can be denoted as "$P_i$", refers to a free phosphate ion in solution, and is distinguished from phosphates bound in various phosphate esters.

A "G1P-producing enzyme" can refer to an enzyme that catalyzes synthesis of products in which at least one product is a G1P. Examples of G1P-producing enzymes include starch phosphorylase, sucrose phosphorylase, and cellodextrin phosphorylase (when catalyzing above reaction in reverse direction, i.e., cellulose hydrolysis).

"Starch phosphorylase" as used herein is of the EC entry 2.4.1.1 and can catalyze conversion of starch and inorganic phosphate to glucose-1-phosphate. Such a reaction can also be written as: (1,4-alpha-D-glucosyl)$_n$+phosphate→(1,4-alpha-D-glucosyl)$_{n-1}$+alpha-D-glucose-1-phosphate, where "(1,4-alpha-D-glucosyl)$_n$" refers to starch.

A "starch debranching enzyme" as used herein refers to an enzyme that can catalyze hydrolysis of 1,6-alpha-D-glucosidic linkages, which are at branch points in starch. Examples of starch debranching enzymes herein include pullulanase and isoamylase. A "pullulanase" as used herein is of the EC entry 3.2.1.41. An "isoamylase" as used herein is of the EC entry 3.2.1.68.

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

"Sucrose phosphorylase" as used herein is of the EC entry 2.4.1.7 and can catalyze conversion of sucrose and phosphate to fructose and G1P. Such a reaction can also be written as: sucrose+phosphate→fructose+alpha-D-glucose-1-phosphate.

"Cellulosic biomass", "cellulose-comprising biomass" and the like are used interchangeably herein and refer to material comprising the structural portion of plants (e.g., wood, stems) that cannot directly be used for food ingredients or as fermentation substrates.

"Endoglucanase" and "beta-1,4-endoglucanase" are used interchangeably herein and refer to an enzyme that can cleave internal bonds within cellulose chains, making shorter cellulose chains. Such shorter chains are suitable substrates for cellodextrin phosphorylase when catalyzing the above reaction in reverse direction (i.e., cellulose hydrolysis).

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

The terms "polynucleotide", "polynucleotide sequence", "nucleic acid sequence" and the like are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a DNA polynucleotide sequence that expresses an RNA (RNA is transcribed from the DNA polynucleotide sequence) from a coding region, which RNA can be a messenger RNA (encoding a protein) or a non-protein-coding RNA. A gene may refer to the coding region alone, or may include regulatory sequences upstream and/or downstream to the coding region (e.g., promoters, 5'-untranslated regions, 3'-transcription terminator regions). A coding region encoding a protein can alternatively be referred to herein as an "open reading frame" (ORF). A gene that is "native" or "endogenous" refers to a gene as found in nature with its own regulatory sequences; such a gene is located in its natural location in the genome of a host cell. A "chimeric" gene refers to any gene that is not a native gene, comprising regulatory and coding sequences that are not found together in nature (i.e., the regulatory and coding regions are heterologous with each other). Accordingly, a chimeric gene may comprise regulatory sequences and coding sequences that are derived from different sources, or regulatory sequences and coding sequences derived from the same source, but arranged in a manner different than that found in nature. A "foreign" or "heterologous" gene refers to a gene that is introduced into the host organism by gene transfer. Foreign/heterologous genes can comprise native genes inserted into a non-native organism, native genes introduced into a new location within the native host, or chimeric genes. The polynucleotide sequences in certain embodiments disclosed herein are heterologous. A "transgene" is a gene that has been introduced into the genome by a gene delivery procedure (e.g., transformation). A "codon-optimized" open reading frame has its frequency of codon usage designed to mimic the frequency of preferred codon usage of the host cell.

A "non-native" amino acid sequence or polynucleotide sequence comprised in a cell or organism herein does not occur in a native (natural) counterpart of such cell or organism.

"Regulatory sequences" as used herein refer to nucleotide sequences located upstream of a gene's transcription start site (e.g., promoter), 5' untranslated regions, introns, and 3' non-coding regions, and which may influence the transcription, processing or stability, and/or translation of an RNA transcribed from the gene. Regulatory sequences herein may include promoters, enhancers, silencers, 5' untranslated leader sequences, introns, polyadenylation recognition sequences, RNA processing sites, effector binding sites, stem-loop structures, and other elements involved in regulation of gene expression. One or more regulatory elements herein (e.g., promoter) may be heterologous to a coding region herein.

The term "operably linked" as used herein refers to the association of two or more nucleic acid sequences such that that the function of one is affected by the other. For example, a promoter is operably linked with a coding sequence when it is capable of affecting the expression of that coding sequence. That is, the coding sequence is under the transcriptional control of the promoter. A coding sequence can be operably linked to one (e.g., promoter) or more (e.g., promoter and terminator) regulatory sequences, for example.

The term "recombinant" when used herein to characterize a DNA sequence such as a plasmid, vector, or construct refers to an artificial combination of two otherwise separated segments of sequence, e.g., by chemical synthesis and/or by manipulation of isolated segments of nucleic acids by genetic engineering techniques. Methods for preparing recombinant constructs/vectors herein can follow standard recombinant DNA and molecular cloning techniques as described by J. Sambrook and D. Russell (*Molecular Cloning: A Laboratory Manual*, 3rd Edition, Cold Spring Harbor Laboratory Press, Cold Spring Harbor, N.Y., 2001); T. J. Silhavy et al. (*Experiments with Gene Fusions, Cold Spring Harbor Laboratory Press, Cold Spring Harbor, N.Y.*, 1984); and F. M. Ausubel et al. (*Short Protocols in Molecular Biology*, 5th Ed. Current Protocols, John Wiley and Sons, Inc., NY, 2002), for example.

The term "transformation" as used herein refers to the transfer of a nucleic acid molecule into a host organism or host cell by any method. A nucleic acid molecule that has been transformed into an organism/cell may be one that replicates autonomously in the organism/cell, or that integrates into the genome of the organism/cell, or that exists transiently in the cell without replicating or integrating. Non-limiting examples of nucleic acid molecules suitable for transformation are disclosed herein, such as plasmids and linear DNA molecules. Host organisms/cells herein containing a transforming nucleic acid sequence can be referred to as "transgenic", "recombinant", "transformed", engineered, as a "transformant", and/or as being "modified for exogenous gene expression", for example.

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. It would be understood that, when calculating sequence identity between a DNA sequence and an RNA sequence, T residues of the DNA sequence align with, and can be considered "identical" with, U residues of the RNA sequence. For purposes of determining "percent complementarity" of first and second polynucleotides, one can obtain this by determining (i) the percent identity between the first polynucleotide and the complement sequence of the second polynucleotide (or vice versa), for example, and/or (ii) the percentage of bases between the first and second polynucleotides that would create canonical Watson and Crick base pairs.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW, ClustalV, or Clustal-Omega). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4. Alternatively still, percent identity between sequences may be performed using an EMBOSS algorithm (e.g., needle) with parameters such as GAP OPEN=10, GAP EXTEND=0.5, END GAP PENALTY=false, END GAP OPEN=10, END GAP EXTEND=0.5 using a BLOSUM matrix (e.g., BLOSUM62).

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. Any polypeptide amino acid sequence disclosed herein beginning with a methionine can optionally be considered without this methionine residue (i.e., a polypeptide sequence can be referred to in reference to the position-2 residue to the C-terminal residue of the sequence).

The term "isolated" as used herein refers to a polynucleotide, polypeptide, or cellulose material that has been completely or partially purified. In some instances, the isolated polynucleotide, polypeptide, or cellulose material is part of a greater composition, buffer system, or reagent mix. For example, the isolated polynucleotide or polypeptide molecule can be comprised within a cell or organism in a heterologous manner. Such a cell or organism containing heterologous components and/or one or more genetic deletions does not occur in nature. Another example is an isolated cellodextrin phosphorylase enzyme or reaction. Cellulose compositions herein and the enzymes and reactions used to produce these compositions are synthetic/man-made, and/or exhibit properties not believed to naturally occur.

An "aqueous composition" herein has a liquid component that comprises at least about 10 wt % water, for example. Examples of aqueous compositions include mixtures, solutions, dispersions (e.g., colloidal dispersions), suspensions and emulsions, for example. An aqueous composition in certain embodiments can comprise an insoluble cellulose as disclosed herein, in which case the aqueous composition can optionally be characterized as a solid-in-liquid composition, given the cellulose insolubility.

As used herein, the term "colloidal dispersion" refers to a heterogeneous system having a dispersed phase and a dispersion medium, i.e., microscopically dispersed insoluble particles are suspended throughout another substance (e.g., an aqueous composition such as water or aqueous solution). An example of a colloidal dispersion herein is a hydrocolloid. All, or a portion of, the particles of a colloidal dispersion such as a hydrocolloid can comprise cellulose of the present disclosure. The terms "dispersant" and "dispersion agent" are used interchangeably herein to refer to a material that promotes the formation and/or stabilization of a dispersion.

The terms "hydrocolloid" and "hydrogel" are used interchangeably herein. A hydrocolloid refers to a colloid system in which water or an aqueous solution is the dispersion medium.

The term "aqueous solution" herein refers to a solution in which the solvent comprises water. An aqueous solution can serve as a dispersant in certain aspects herein. Cellulose in certain embodiments can be dispersed or mixed within an aqueous solution.

The term "viscosity" as used herein refers to the measure of the extent to which a fluid or an aqueous composition such as a hydrocolloid resists a force tending to cause it to flow. Various units of viscosity that can be used herein include centipoise (cPs) and Pascal-second (Pa·s). A centipoise is one one-hundredth of a poise; one poise is equal to 0.100 kg·m$^{-1}$·s$^{-1}$, or 1 mPa·s. Thus, the terms "viscosity modifier", "viscosity-modifying agent" and the like as used herein refer to anything that can alter/modify the viscosity of a fluid or aqueous composition.

The term "shear thinning behavior" as used herein refers to a decrease in the viscosity of an aqueous composition as shear rate increases. "Shear rate" herein refers to the rate at which a progressive shearing deformation is applied to an aqueous composition. A shearing deformation can be applied rotationally, for example.

The term "contacting" as used herein with respect to methods of increasing the viscosity of an aqueous composition refers to any action that results in bringing together an aqueous composition with cellulose as presently disclosed. Contacting can be performed by any means known in the art, such as mixing, shaking, or homogenization, for example.

"DMSO" as used herein refers to dimethyl sulfoxide, which has the formula $(CH_3)_2SO$.

"DMAc" as used herein refers to N,N-dimethylacetamide, which has the formula $CH_3CON(CH_3)_2$.

The terms "mercerization", "mercerization process" and the like are used interchangeably herein to refer to a process in which cellulose material is treated under caustic alkali conditions, typically comprising sodium hydroxide. Cellulose as disclosed in certain embodiments herein has not been mercerized.

The terms "derivatization", "derivatization process" and the like are used interchangeably herein to refer to a process in which cellulose material is treated under conditions leading to the substitution of one or more hydrogens of cellulose —OH groups with a different moiety/functional group (e.g., carboxymethyl group). Cellulose as disclosed in certain embodiments herein has not been derivatized.

The term "film" as used herein refers to a thin, visually continuous material. A film can be comprised as a thin layer or coating on a material, or can be alone (e.g., not attached to a material surface). A "coating" as used herein refers to a thin layer covering a surface of a material.

The term "uniform thickness" as used to characterize a film or coating herein can refer to a contiguous area that (i) is at least 20% of the total film/coating area, and (ii) has a standard deviation of thickness of less than about 50 nm, for example.

A film or coating herein can be characterized as being of "low permeability" to a particular substance if the film/coating permeability to the substance is below a threshold value commonly assigned in the art of interest. To illustrate, the threshold value for styrene permeability in the SMC (super-multicoated) release film field is $200 \times 10^{-9}$ g cm/cm$^2$/h, such as measured using the method described in *American Institute of Chemical Engineer, 53rd National Meeting, Preprint No. 32d* (Bixler and Michaels, 1964). A film or coating can be characterized as being "impermeable" to a particular substance if it does not permit passage of the substance over an extended period of time (e.g., one or more days).

Development of new forms of cellulose is desirable given the potential utility thereof in various applications. The development of novel enzymatic processes may be a useful means for producing new types of cellulose material.

Embodiments of the present disclosure concern an enzymatic reaction comprising at least water, glucose-1-phosphate, cellodextrin, and a cellodextrin phosphorylase enzyme that synthesizes cellulose. For example, a cellodextrin phosphorylase enzyme can (i) comprise an amino acid sequence that is at least 90% identical to SEQ ID NO:2 or SEQ ID NO:6, and (ii) synthesize cellulose. Significantly, such enzymatic reactions are able to produce low molecular weight, insoluble cellulose that has enhanced features under both dry and aqueous conditions, rendering such cellulose as having broad applicability.

An enzyme with cellodextrin phosphorylase activity suitable for use in an enzymatic reaction as presently disclosed can comprise, for example, an amino acid sequence that is at least 90% identical to SEQ ID NO:2 or SEQ ID NO:6. In some embodiments, such an enzyme can comprise, or consist of, an amino acid sequence that is 100% identical to, or at least 90%, 91%, 92%, 93%, 94%, 95%, 96%, 97%, 98%, or 99% identical to, SEQ ID NO:2 or SEQ ID NO:6. Non-limiting examples of a cellodextrin phosphorylase enzyme comprising SEQ ID NO:2 include cellodextrin phosphorylase enzymes comprising, or consisting of, an amino acid sequence that is 100% identical to, or at least 90%, 91%, 92%, 93%, 94%, 95%, 96%, 97%, 98%, or 99% identical to, SEQ ID NO:4. Non-limiting examples of a cellodextrin phosphorylase enzyme comprising SEQ ID NO:6 include cellodextrin phosphorylase enzymes comprising, or consisting of, an amino acid sequence that is 100% identical to, or at least 90%, 91%, 92%, 93%, 94%, 95%, 96%, 97%, 98%, or 99% identical to, SEQ ID NO:8. A variant cellodextrin phosphorylase enzyme (e.g., between 90-99% amino acid identity with SEQ ID NO:2, 4, 6, or 8 reference sequence) should have some of (e.g., at least 30%, 40%, 50%, 60%, 70%, 80%, or 90% of), or all of, the enzymatic activity (refer to above definitions) of the corresponding non-variant reference sequence.

A polynucleotide sequence encoding SEQ ID NO:2 or SEQ ID NO:4 can optionally comprise a nucleotide sequence that is 100% identical to, or at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, SEQ ID NO:1 or 3, respectively. A polynucleotide sequence encoding SEQ ID NO:6 or SEQ ID NO:8 can optionally comprise a nucleotide sequence that is 100% identical to, or at least 70%, 71%, 72%, 73%, 74%, 75%, 76%, 77%, 78%, 79%, 80%, 81%, 82%, 83%, 84%, 85%, 86%, 87%, 88%, 89%, 90%, 91% 92%, 93%, 94%, 95%, 96%, 97%, 98%, or 99% identical to, SEQ ID NO:5 or 7, respectively.

Given that certain amino acids share similar structural and/or charge features with each other (i.e., conserved), one or more amino acids of a cellodextrin phosphorylase sequence herein (and/or other types of polypeptides herein) can be substituted with a conserved amino acid residue ("conservative amino acid substitution") as follows:

1. The following small aliphatic, nonpolar or slightly polar residues can substitute for each other: Ala (A), Ser (S), Thr (T), Pro (P), Gly (G);
2. The following polar, negatively charged residues and their amides can substitute for each other: Asp (D), Asn (N), Glu (E), Gln (Q);
3. The following polar, positively charged residues can substitute for each other: His (H), Arg (R), Lys (K);
4. The following aliphatic, nonpolar residues can substitute for each other: Ala (A), Leu (L), Ile (I), Val (V), Cys (C), Met (M); and
5. The following large aromatic residues can substitute for each other: Phe (F), Tyr (Y), Trp (W).

An enzyme with cellodextrin phosphorylase activity herein can be obtained from any microbial source, for example, such as a bacteria or fungus (e.g., yeast). Examples of suitable bacteria include *Vibrio* species and *Ruminococcus* species. Examples of suitable *Vibrio* species include *V. ruber, V. cholerae, V. adaptatus, V. alginolyticus, V. mimicus, V. parahaemolyticus, V. proteolyticus,* and *V. vulnificus.* Examples of suitable *Ruminococcus* species include *R. champanellensis, R. albus, R. bromii, R. flavefaciens, R. gnavus, R. lactaris, R. obeum,* and *R. torques.*

Examples of enzymes with cellodextrin phosphorylase activity herein can be any of the amino acid sequences disclosed herein and that further include 1-300 (or any integer there between [e.g., 10, 15, 20, 25, 30, 35, 40, 45, or 50]) residues on the N-terminus and/or C-terminus. Such additional residues may be a heterologous sequence such as an epitope tag (at either N- or C-terminus) (e.g., His tag such as a hexa histidine) or a heterologous signal peptide (at N-terminus), for example. In those embodiments in which a heterologous amino acid sequence is incorporated at the N-terminus, such a heterologous sequence can be adjacent to the original start-methionine of the cellodextrin phosphorylase, or can replace the original start methionine, for example. In the latter embodiment, a new start-methionine can be employed at the N-terminus of the added heterologous sequence.

An enzyme with cellodextrin phosphorylase activity as presently disclosed typically lacks an N-terminal signal peptide. However, an expression system for producing a cellodextrin phosphorylase enzyme can optionally employ an enzyme-encoding polynucleotide that further comprises sequence encoding an N-terminal signal peptide to direct extra-cellular secretion. The signal peptide in such embodiments is cleaved from the enzyme during the secretion process. Since it is believed that the cellodextrin phosphorylase enzymes disclosed herein (e.g., SEQ ID NO:2 and 6) are not associated with a signal peptide as natively expressed, any added signal peptide may be considered as heterologous to the enzyme. An example of a signal peptide useful herein is one from a bacterial (e.g., a *Bacillus* species such as *B. subtilis*) or fungal species. An example of a bacterial signal peptide is an aprE signal peptide, such as one from *Bacillus* (e.g., *B. subtilis*, see Vogtentanz et al., *Protein Expr. Purif.* 55:40-52, which is incorporated herein by reference).

A cellodextrin phosphorylase enzyme in some embodiments does not occur in nature; for example, an enzyme herein is not believed to be one that is naturally secreted (i.e., mature form) from a microbe (from which the cellodextrin phosphorylase enzyme herein could possibly have been derived).

A cellodextrin phosphorylase enzyme herein can be prepared by fermentation of an appropriately engineered microbial strain, for example. Recombinant enzyme production by fermentation is well known in the art using microbial strains such as *E. coli, Bacillus* strains (e.g., *B. subtilis*), *Ralstonia eutropha, Pseudomonas fluorescens, Saccharomyces cerevisiae, Pichia pastoris, Hansenula polymorpha,* and species of *Aspergillus* (e.g., *A. awamori*) and *Trichoderma* (e.g., *T. reesei*) (e.g., see Adrio and Demain, *Biomolecules* 4:117-139, which is incorporated herein by reference).

A cellodextrin phosphorylase enzyme of the present disclosure may be used in any purification state (e.g., pure or non-pure). For example, a cellodextrin phosphorylase enzyme may be purified and/or isolated prior to its use. Examples of cellodextrin phosphorylase enzymes that are non-pure include those in the form of a cell lysate. A cell lysate or extract may be prepared from a bacteria (e.g., *E. coli*) used to heterologously express the enzyme. For example, the bacteria may be subjected to disruption using a French pressure cell. In alternative embodiments, bacteria may be homogenized with a homogenizer (e.g., APV, Rannie, Gaulin). A cellodextrin phosphorylase enzyme is typically soluble in these types of preparations. A bacterial cell lysate, extract, or homogenate herein may be used at about 0.15-0.3% (v/v) in an enzymatic reaction herein, if desired. In other embodiments, an enzyme with cellodextrin phosphorylase activity can be isolated after its expression. For example, the enzyme can be isolated using a binding/washing or binding/washing/elution approach (e.g., binding enzyme to a column of other fixed surface, followed by washing and optionally eluting enzyme off column or other fixed surface). An enzyme isolation approach can comprise binding a heterologous amino acid sequence-tagged cellodextrin phosphorylase enzyme in certain embodiments, wherein such binding is via the heterologous amino acid sequence tag (e.g., His tag). A cellodextrin phosphorylase enzyme can be isolated from a cell lysate or any other composition (e.g., medium into which enzyme is optionally secreted), for example. In certain aspects, a cellodextrin phosphorylase preparation can lack glucose-1-phosphatase activity. A cellodextrin phosphorylase enzyme in some aspects can be immobilized (e.g., to a matrix) or expressed on cell surfaces. A cellodextrin phosphorylase enzyme can optionally be modified with polyethylene glycol (PEG), for instance.

Cellodextrin phosphorylase enzyme of the present disclosure can synthesize low molecular weight cellulose that is insoluble in aqueous compositions. For example, a cellodextrin phosphorylase as employed in an enzymatic reaction herein can produce low molecular weight, insoluble cellulose.

Cellulose produced by a cellodextrin phosphorylase enzyme in certain embodiments can have a $DP_w$ or $DP_n$ of about 10-1000. For example, $DP_w$ or $DP_n$ of cellulose herein can be about 10-500, 10-250, 10-100, 10-75, 10-50, 10-45, 10-40, 10-35, 10-30, 10-25, 15-50, 15-45, 15-40, 15-35, 15-30, or 15-25. $DP_w$ or $DP_n$ of cellulose in some aspects can be about, at least about, or less than about, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Cellulose produced by a cellodextrin phosphorylase enzyme in some aspects can have an $M_w$ of about 1700-170000, 1700-86000, 1700-43000, 1700-17000, 1700-13000, 1700-8500, 1700-6800, 1700-5100, 2550-5100, or 2550-4250. $M_w$ can be about, at least about, or less than about, 1700, 1900, 2100, 2300, 2500, 2700, 2900, 3100, 3300, 3500, 3700, 3900, 4100, 4300, 4500, 4700, 4900, or 5100 in some aspects.

About 100% of the glycosidic linkages of cellulose produced by a cellodextrin phosphorylase enzyme herein are beta-1,4 linkages, for example. Cellulose in other aspects can have a glycosidic linkage profile of at least about 90%, 91%, 92%, 93%, 94%, 95%, 96%, 97%, 98%, or 99% beta-1,4 linkages. Accordingly, cellulose enzymatically produced herein can have, for example, less than 10%, 9%, 8%, 7%, 6%, 5%, 4%, 3%, 2%, or 1% of glycosidic linkages that are other than beta-1,4.

The backbone of a cellulose synthesized by cellodextrin phosphorylase enzyme herein can be linear/unbranched. Alternatively, there can be branches in the cellulose. Thus, in certain embodiments, cellulose can have no branch points or less than about 5%, 4%, 3%, 2%, or 1% branch points as a percent of the glycosidic linkages in the polymer.

Cellulose produced by a cellodextrin phosphorylase enzyme in some aspects herein can have a cellulose II crystal structure. For example, cellulose herein can comprise about 100% cellulose, by weight, that is of a cellulose II crystal structure. As other examples, cellulose can comprise at least about 80%, 81%, 82%, 83%, 84%, 85%, 86%, 87%, 88%, 89%, 90%, 91%, 92%, 93%, 94%, 95%, 96%, 97%, 98%, or 99% cellulose, by weight, that is of a cellulose II crystal structure. Cellulose in some aspects can comprise less than about 20%, 19%, 18%, 17%, 16%, 15%, 14%, 13%, 12%, 11%, 10%, 9%, 8%, 7%, 6%, 5%, 4%, 3%, 2%, or 1% cellulose material, by weight, that is of a cellulose I, III, and/or IV crystal structure. Cellulose II crystal structure has been described by Kolpak and Blackwell (*Macromolecules* 9:273-278) and Kroon-Batenburg and Kroon (*Glycoconjugate J.* 14:677-690), for example, both of which are incorporated herein by reference. The dominant hydrogen bonds characterizing a cellulose II structure are O2-H—O6, O6-H—O6 and O2-H—O2, whereas cellulose I has O2-H—O6 as a dominant hydrogen bond. The structure of cellulose II comprises chain folding and is difficult to unravel.

Cellulose is produced by a cellodextrin phosphorylase enzyme of the present disclosure directly as cellulose II. In contrast to cellulose as presently disclosed, cellulose produced in nature (e.g., in plants) typically is of a cellulose I structure and generally requires mercerization and/or other chemical treatments (e.g., derivatization followed by underivatization, formation of regenerated cellulose) to convert it into cellulose II. Cellulose in certain embodiments herein is in the cellulose II crystal state under both aqueous and dry conditions.

Cellulose as produced herein is insoluble in aqueous solvents such as water. However, it can be soluble in solvents comprising dimethyl sulfoxide (DMSO) and/or N,N-dimethylacetamide (DMAc). Examples of such solvents include DMSO or DMAc alone or further comprising lithium chloride (LiCl) (e.g., DMSO/LiCl and DMAc/LiCl). A DMSO/LiCl solvent or DMSO/LiCl solvent herein can comprise about 0.5, 1, 2, 3, 4, 5, 6, 7, 8, 9, or 10 wt % LiCl, for example, or can be LiCl-saturated. The concentration of cellulose herein can be at about 0.1-30 wt %, 0.1-20 wt %, 0.1-10 wt %, or 0.1-5 wt %, for example, or can be at about, or at least about, 0.1, 0.3, 0.5, 1, 2, 3, 4, 5, 6, 7, 8, 9, 10, 15, 20, 25, or 30 wt % in a non-aqueous solvent such as one comprising DMSO and/or DMAc. DMSO- and DMAc-comprising solvents herein do not further comprise an acid in certain aspects. Cellulose herein can be dissolved in any of the foregoing DMSO- and DMAc-based solvents at a relatively low temperature, such as at 15-30° C., 20-30° C., or 20-25° C. (e.g., room temperature), for example. In preferred embodiments, heat does not need to be applied to dissolve the cellulose.

Enzymatic reactions of the present disclosure comprise cellodextrin. Examples of cellodextrin suitable for use in an enzymatic reaction herein include cellobiose (DP2), cellotriose (DP3), cellotetraose (DP4), cellopentaose (DP5), and cellohexaose (DP6). Cellobiose is used as a cellodextrin in certain aspects. Other examples of cellodextrin suitable herein include glucose polymers of 7 or more beta-1,4-linked glucose monomers resulting from the breakdown (e.g., enzymatic breakdown) of cellulose. One or more (e.g., a mixture of 2, 3, 4 or more) of the above types of cellodextrin can be employed in some embodiments. Non-phosphorylated glucose monomer typically is not used in an enzymatic reaction herein.

The temperature of an enzymatic reaction herein comprising a cellodextrin phosphorylase enzyme can be controlled, if desired. In certain embodiments, the temperature is between about 5° C. to about 50° C. The temperature in certain other embodiments is between about 20° C. to about 40° C. In still other embodiments, the temperature may be about 20, 21, 22, 23, 24, 25, 26, 27, 28, 29, 30, 31, 32, 33, 34, 35, 36, 37, 38, 39, or 40° C. The temperature of an enzymatic reaction can be maintained using various means known in the art. For example, the temperature can be maintained by placing the vessel containing the reaction in an air or water bath incubator set at the desired temperature.

The pH of an enzymatic reaction in certain embodiments herein can be between about 5.0 to about 9.0. Alternatively, the pH can be about 5.0, 5.5, 6.0, 6.5, 7.0, 7.5, 8.0, 8.5, or 9.0. The pH can be adjusted or controlled by the addition or incorporation of a suitable buffer, including but not limited to: phosphate, tris, citrate, or a combination thereof. Buffer concentration in the enzymatic reaction can be from 0 mM to about 100 mM, or about 10, 25, 50, or 75 mM, for example.

The initial concentration of glucose-1-phosphate (G1P) in the presently disclosed cellodextrin phosphorylase reaction can be about, or at least about, 1 to 100 mM, for example. Other G1P initial concentrations can be, for example, about, or at least about, 1, 5, 10, 20, 30, 40, 50, 60, 70, 80, 90, or 100 mM, or about 10-50 mM. The initial concentration of cellodextrin (e.g., cellobiose) in the presently disclosed cellodextrin phosphorylase reaction can be about 1 to 50 mM, for example. Other cellodextrin initial concentrations can be, for example, about 1, 5, 10, 15, 20, 25, 30, 35, 40, 45, or 50 mM, or about 5-10 mM. "Initial concentration" of a substrate such as G1P or cellodextrin refers to the substrate concentration in an enzymatic reaction just after all the reaction components have been added (at least water, G1P, cellodextrin, cellodextrin phosphorylase enzyme).

The activity of a cellodextrin phosphorylase enzyme herein can be about 1 to 30 units per mg enzyme protein in some embodiments. Enzyme activity can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 10-20, or 15-20 units per mg of enzyme protein, for example. Cellodextrin phosphorylase enzyme activity can be determined using any method known in the art. A unit of cellodextrin phosphorylase activity can refer to, for example, the amount of enzyme that releases 1 micro-mol of inorganic phosphorus (released from cellobiose) per minute under the following conditions: ~10 mM G1P, ~5 mM cellobiose, ~25 mM Tris-HCl buffer, ~pH 7.0, held at ~37° C., optionally for ~10 minutes. Inorganic phosphate release from cellobiose can be gauged using a reagent or kit designed to detect free phosphate (e.g., PiBlue™ Phosphate Assay Kit, BioAssay Systems, Hayward, Calif.).

The amount of a cellodextrin phosphorylase enzyme comprised in an enzymatic reaction in some aspects can be about 0.1-2.0 or 0.5-1.0 units/m L. For example, at least about 0.2, 0.4, 0.6, 0.7, 0.8, 0.9, 1.0, 1.2, 1.4, 1.6, 1.8, or 2.0 units/mL of enzyme can be employed in a reaction.

Embodiments of the present disclosure also concern a method for producing cellulose, comprising:

a) contacting at least water, glucose-1-phosphate (G1P), cellodextrin, and a cellodextrin phosphorylase enzyme (e.g., one comprising an amino acid sequence that is at least 90% identical to SEQ ID NO:2 or SEQ ID NO:6), wherein insoluble cellulose is produced; and b) optionally, isolating the cellulose produced in step (a).

The contacting step in a method herein of producing cellulose can optionally be characterized as providing an enzymatic reaction comprising water, glucose-1-phosphate, cellodextrin, and a cellodextrin phosphorylase enzyme of the present disclosure. The contacting step in a cellulose production method herein can be performed in any number of ways. For example, the desired amount of G1P and/or cellodextrin (e.g., cellobiose) can first be dissolved in water (optionally, other components may also be added at this stage of preparation, such as buffer components), followed by addition of one or more cellodextrin phosphorylase enzymes. The reaction may be kept still, or agitated via stirring or orbital shaking, for example. The reaction can be, and typically is, cell-free.

The enzymatic reaction of a cellulose production method can be contained within any vessel suitable for applying one or more of the reaction conditions disclosed herein. For example, a stainless steel, plastic, or glass vessel or container of a size suitable to contain a particular reaction can be employed. Such a vessel can optionally be equipped with a stirring device.

Completion of an enzymatic reaction of a cellulose production method in certain embodiments can be determined visually (e.g., no more accumulation of insoluble cellulose) and/or by measuring the amount of substrate (G1P and/or cellodextrin) left in the reaction (e.g., no more decrease in substrate levels over time). Typically, a reaction of the disclosed method can take about 12, 18, 24, 30, 36, 48, 60, 72, 84, or 96 hours to complete, for example. Reaction time may depend, for example, on certain parameters such as the amount of substrate and/or cellodextrin phosphorylase enzyme employed.

Insoluble cellulose produced in the disclosed method may optionally be isolated. For example, insoluble cellulose may be separated by centrifugation or filtration. In doing so, the cellulose is separated from the reaction solution, which can comprise water, residual substrate(s) and reaction byproducts.

Insoluble cellulose produced in a contacting step of a cellulose production method herein can have any of the features disclosed herein. For example, any of the features of water-insolubility, $DP_w$ (e.g., $DP_w$ of 10-30) and/or $M_w$, glycosidic linkage profile, backbone structure (e.g., linearity), cellulose II structural content, and/or solubility in certain non-aqueous compositions as disclosed elsewhere herein can characterize cellulose produced in step (a).

Insoluble cellulose produced in a contacting step of a cellulose production method in some aspects can have a cellulose II crystal structure (i.e., the cellulose is enzymatically synthesized directly as cellulose II). In contrast to cellulose as presently disclosed, cellulose produced in nature (e.g., in plants) typically is of a cellulose I structure and generally requires mercerization and/or other chemical treatments (e.g., derivatization followed by un-derivatization, formation of regenerated cellulose) to convert it into cellulose II. Cellulose in certain embodiments herein is in the cellulose II crystal state under both aqueous and dry conditions.

Any features disclosed herein characterizing enzymatic reaction embodiments can be employed in performing a contacting step of a cellulose production method. For example, any of the features of cellodextrin phosphorylase enzyme amino acid sequence and source, substrate levels, temperature, pH and buffer levels, and/or enzyme activity/amount as disclosed elsewhere herein can characterize a reaction performed in the contacting step.

The contacting step of a cellulose production method in some aspects can comprise cellobiose as a cellodextrin. Other examples of cellodextrin suitable for use in an enzymatic reaction herein include cellotriose, cellotetraose, cellopentaose, and cellohexaose. Still other examples of cellodextrin suitable herein include glucose polymers of 7 or more beta-1,4-linked glucose monomers resulting from the breakdown (e.g., enzymatic breakdown) of cellulose. One or more (e.g., a mixture of 2, 3, 4 or more) of the above types of cellodextrin can be employed in some embodiments.

Glucose-1-phosphate (G1P) provided in a contacting step of a cellulose production method can be providing directly via addition of isolated G1P (e.g., G1P obtained from a commercial source), for example. Alternatively, G1P can be provided in the contacting step by providing at least a second reaction, wherein the products of the second reaction comprise G1P (i.e., the second reaction produces G1P as a product). A "second reaction" refers to a reaction that is in addition to the cellodextrin phosphorylase reaction performed in the contacting step (can optionally be denoted as a "first reaction"), and which provides G1P substrate for the cellodextrin phosphorylase reaction. A second reaction can optionally be characterized as employing a "G1P-producing enzyme" such as a starch phosphorylase, sucrose phosphorylase, or cellodextrin phosphorylase (when catalyzing cellulose hydrolysis).

A second reaction for providing G1P in some aspects can be provided in the same vessel in which a cellodextrin phosphorylase enzymatic reaction is performed. Alternatively, a second reaction can be performed outside of (separate from) the vessel in which a cellodextrin phosphorylase enzymatic reaction is performed. A second reaction can be performed before and/or continuously with a cellodextrin phosphorylase enzymatic reaction of a cellulose production method.

A second reaction in some embodiments can comprise contacting water, inorganic phosphate, starch, a starch phosphorylase, and optionally a starch debranching enzyme such as a pullulanase and/or an isoamylase. This type of second reaction can optionally be characterized as a starch phosphorylase reaction. Starch phosphorylases (EC 2.4.1.1) suitable for use herein include those disclosed in U.S. Patent Appl. Publ. No. 2002/0133849 and Tiwari and Kumar (*Biotechnol. Mol. Biol. Rev.* 7:69-83), for example, which are incorporated herein by reference. A starch phosphorylase in some aspects can be a plant, microbial (e.g., bacterial), or fungal (e.g., yeast) starch phosphorylase. Pullulanases (EC 3.2.1.41) suitable for use herein include those disclosed in U.S. Pat. Nos. 8,354,101, 7,906,306, 7,449,320, and 7,399,623, for example, which are incorporated herein by reference. A pullulanase in some aspects can be a plant, microbial (e.g., bacterial), or fungal (e.g., yeast) pullulanase. Isoamylases (EC 3.2.1.68) suitable for use herein include those disclosed in U.S. Pat. Nos. 5,352,602, 5,811,277, 7,615,365 and 8,735,105, for example, which are incorporated herein by reference. An isoamylase in some aspects can be a plant, microbial (e.g., bacterial), or fungal (e.g., yeast) isoamylase.

A second reaction in some embodiments can comprise contacting water, inorganic phosphate, sucrose, and a sucrose phosphorylase enzyme. This type of second reaction can optionally be characterized as a sucrose phosphorylase reaction. Sucrose phosphorylases (EC 2.4.1.7) suitable for use herein include those disclosed in U.S. Pat. Nos. 5,716,837, 7,229,801 and 7,968,309, for example, which are incorporated herein by reference. A sucrose phosphorylase in some aspects can be a plant, microbial (e.g., bacterial), or fungal (e.g., yeast) sucrose phosphorylase.

A second reaction in some embodiments can comprise contacting water, inorganic phosphate, cellulosic biomass (cellulose-comprising biomass such as lignocellulosic biomass), an endoglucanase, a cellodextrin phosphorylase, and optionally, a lytic polysaccharide monooxygenase and/or a cellobiohydrolase. Endoglucanases (e.g., cellulase, beta-1,4-glucanase) suitable for use herein include those disclosed in U.S. Pat. Nos. 4,435,307, 5,776,757 and 7,604,974, for example, which are incorporated herein by reference. An endoglucanase (e.g., cellulase) in some aspects can be a plant, microbial (e.g., bacterial), or fungal (e.g., yeast) endoglucanase. A cellodextrin phosphorylase suitable for use herein can be any cellodextrin phosphorylase as presently disclosed, or as disclosed in U.S. Pat. No. 8,889,379, or U.S. Patent Appl. Publ. Nos. 2014/0087435, 2014/0057323, and 2013/0059340, for example, which are incorporated herein by reference. This type of second reaction (i.e., endoglucanase+cellodextrin phosphorylase) can typically be performed separately from a cellodextrin phosphorylase enzymatic reaction of a cellulose production method herein. Lytic polysaccharide monooxygenases suitable for use herein include those disclosed in Isaksen et al. (*J. Biol. Chem.* 289:2632-2642) and Eibinger et al. (*J. Biol. Chem.*, Oct. 31, 2014, pii: jbc.M114.602227 [Epub ahead of print]), for example, which are incorporated herein by reference.

Embodiments of the present disclosure further concern a composition comprising an enzyme comprising an amino acid sequence that is at least 90% identical to SEQ ID NO:2, wherein the enzyme has cellodextrin phosphorylase activity. Significantly, such an enzyme is able to produce a low molecular weight, insoluble cellulose that has enhanced features under both dry and aqueous conditions, rendering such cellulose as having broad applicability. A non-limiting example of a composition comprising a cellodextrin phosphorylase enzyme having an amino acid sequence that is at least 90% identical to SEQ ID NO:2 is an enzymatic reaction, such as one also comprising at least water, glucose-1-phosphate, and one or more cellodextrins.

An enzyme herein with cellodextrin phosphorylase activity can comprise an amino acid sequence that is at least 90% identical to SEQ ID NO:2. In other embodiments, such an enzyme can comprise, or consist of, an amino acid sequence that is 100% identical to, or at least 90%, 91%, 92%, 93%, 94%, 95%, 96%, 97%, 98%, or 99% identical to, SEQ ID NO:2. Non-limiting examples of a cellodextrin phosphorylase enzyme comprising SEQ ID NO:2 include cellodextrin phosphorylase enzymes comprising, or consisting of, an amino acid sequence that is 100% identical to, or at least 90%, 91%, 92%, 93%, 94%, 95%, 96%, 97%, 98%, or 99% identical to, SEQ ID NO:4. A variant cellodextrin phosphorylase enzyme (e.g., between 90-99% amino acid identity with SEQ ID NO:2 or 4 reference sequence) should have some of (e.g., at least 30%, 40%, 50%, 60%, 70%, 80%, or 90% of), or all of, the enzymatic activity (refer to above definitions) of the corresponding non-variant reference sequence.

An enzyme with cellodextrin phosphorylase activity of the present disclosure can, optionally, synthesize cellulose in a reaction comprising water, glucose-1-phosphate, and cellodextrin. Cellulose produced in such a reaction can be insoluble (water-insoluble) and have a weight-average degree of polymerization ($DP_w$) of about 10 to about 30.

Certain aspects herein concern a polynucleotide sequence comprising a nucleotide sequence encoding a cellodextrin phosphorylase comprising an amino acid sequence that is at least 90% identical to SEQ ID NO:2. Any such amino acid sequence as disclosed herein, for example, can be encoded by the nucleotide sequence. The nucleotide sequence may optionally be in operable linkage with a promoter sequence (e.g., heterologous promoter). Some embodiments include, for example, a polynucleotide (e.g., vector or construct) comprising at least one open reading frame encoding a cellodextrin phosphorylase comprising an amino acid sequence that is at least 90% identical to SEQ ID NO:2. Such a coding region can optionally be operably linked to a promoter sequence (e.g., heterologous promoter) suitable for expression in a cell (e.g., bacteria cell; eukaryotic cell such as a yeast, insect, or mammalian cell) or in an in vitro protein expression system, for example. Examples of a vector or construct include circular (e.g., plasmid) and non-circular (e.g., linear DNA such as an amplified DNA sequence) polynucleotide molecules.

Certain embodiments herein concern a method of producing a cellodextrin phosphorylase comprising an amino acid sequence that is at least 90% identical to SEQ ID NO:2. This method can comprise the steps of: providing a polynucleotide sequence having a nucleotide sequence encoding a cellodextrin phosphorylase comprising an amino acid sequence that is at least 90% identical to SEQ ID NO:2 (e.g., any such amino acid sequence as disclosed herein), and expressing the cellodextrin phosphorylase from the polynucleotide sequence, thereby producing the cellodextrin phosphorylase. The expression step in such a method can optionally be performed in a cell (e.g., bacteria cell such as *E. coli*; eukaryotic cell such as a yeast [e.g., *S. cerevisiae*], insect, or mammalian cell). Alternatively, expression of can be performed in an in vitro protein expression system (e.g., cell-free protein expression systems such as those employing rabbit reticulocyte lysate or wheat germ extract). Also, cellodextrin phosphorylase produced in the expression step can optionally be isolated. Such isolation can be performed in a manner that produces a composition having any of the features disclosed herein (e.g., purity, pH, buffer, and/or salt level), for example.

Embodiments of the present disclosure further concern a composition comprising cellulose, wherein the cellulose:
(i) has a weight-average degree of polymerization ($DP_w$) of about 10 to about 1000,
(ii) has a cellulose II crystal structure, and
(iii) is insoluble in an aqueous composition.

Significantly, such low molecular weight, insoluble cellulose has broad utility, owing to its having enhanced features under both dry and aqueous conditions as further disclosed herein.

Cellulose of a composition as presently disclosed is of low molecular weight cellulose and water-insoluble. Cellulose in certain embodiments can have a $DP_w$ or $DP_n$ of about 10-1000. For example, $DP_w$ or $DP_n$ of cellulose herein can be about 10-500, 10-250, 10-100, 10-75, 10-50, 10-45, 10-40, 10-35, 10-30, 10-25, 15-50, 15-45, 15-40, 15-35, 15-30, or 15-25. $DP_w$ or $DP_n$ of cellulose in some aspects can be about, or at least about, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In some aspects herein, cellulose can have an $M_w$ of about 1700-170000, 1700-86000, 1700-43000, 1700-17000, 1700-13000, 1700-8500, 1700-6800, 1700-5100, 2550-5100, or 2550-4250. $M_w$ can be about, or at least about, 1700, 1900, 2100, 2300, 2500, 2700, 2900, 3100, 3300, 3500, 3700, 3900, 4100, 4300, 4500, 4700, 4900, or 5100 in some examples.

About 100% of the glycosidic linkages of cellulose as presently disclosed are beta-1,4 linkages, for example. Cellulose in other aspects can have a glycosidic linkage profile of at least about 90%, 91%, 92%, 93%, 94%, 95%, 96%, 97%, 98%, or 99% beta-1,4 linkages. Accordingly, cellulose herein can have, for example, less than 10%, 9%, 8%, 7%, 6%, 5%, 4%, 3%, 2%, or 1% of glycosidic linkages that are other than beta-1,4.

The backbone of cellulose disclosed herein can be linear/unbranched. Alternatively, there can be branches in the cellulose. Thus, in certain embodiments, cellulose can have no branch points or less than about 5%, 4%, 3%, 2%, or 1% branch points as a percent of the glycosidic linkages in the polymer.

Cellulose as disclosed herein can have a cellulose II crystal structure. For example, cellulose herein can comprise about 100% cellulose, by weight, that is of a cellulose II crystal structure. As other examples, cellulose can comprise at least about 80%, 81%, 82%, 83%, 84%, 85%, 86%, 87%, 88%, 89%, 90%, 91%, 92%, 93%, 94%, 95%, 96%, 97%, 98%, or 99% cellulose, by weight, that is of a cellulose II crystal structure. Cellulose in some aspects can comprise less than about 20%, 19%, 18%, 17%, 16%, 15%, 14%, 13%, 12%, 11%, 10%, 9%, 8%, 7%, 6%, 5%, 4%, 3%, 2%, or 1% cellulose material, by weight, that is of a cellulose I, III, and/or IV crystal structure. Cellulose II crystal structure has been described by Kolpak and Blackwell (*Macromolecules* 9:273-278) and Kroon-Batenburg and Kroon (*Glycoconjugate J.* 14:677-690), for example, both of which are incorporated herein by reference. The dominant hydrogen bonds characterizing a cellulose II structure are O2-H—O6, O6-H—O6 and O2-H—O2, whereas cellulose I has O2-H—O6 as a dominant hydrogen bond. The structure of cellulose II comprises chain folding and is difficult to unravel.

Cellulose herein can be characterized as being isolated, for example. Compositions comprising cellulose as presently disclosed are not believed to occur in nature.

Cellulose as disclosed herein can optionally be characterized as having a flake or flake-like shape at nanometer scale. Flake or flake-like shapes formed by the cellulose have nano-size dimensions; such shapes can appear as flat, thin pieces of material when using appropriate microscopic techniques such as disclosed in the present Examples. In other aspects, cellulose herein is not, nor has been, derivatized. Thus, cellulose as disclosed herein does not comprise added functional groups such as ether groups (e.g., carboxymethyl groups) or ester groups (e.g., acetate groups).

Cellulose of a composition as presently disclosed herein can be a product of a cellodextrin phosphorylase enzyme comprising, or consisting of, an amino acid sequence that is at least 90% identical to SEQ ID NO:2 or SEQ ID NO:6. In other embodiments, cellulose can be a product of a cellodextrin phosphorylase enzyme that comprises, or consists of, an amino acid sequence that is 100% identical to, or at least 90%, 91%, 92%, 93%, 94%, 95%, 96%, 97%, 98%, or 99% identical to, SEQ ID NO:2 or SEQ ID NO:6. Non-limiting examples of a cellodextrin phosphorylase enzyme comprising SEQ ID NO:2 include cellodextrin phosphorylase enzymes comprising, or consisting of, an amino acid sequence that is 100% identical to, or at least 90%, 91%, 92%, 93%, 94%, 95%, 96%, 97%, 98%, or 99% identical to, SEQ ID NO:4. Non-limiting examples of a cellodextrin phosphorylase enzyme comprising SEQ ID NO:6 include cellodextrin phosphorylase enzymes comprising, or consisting of, an amino acid sequence that is 100% identical to, or at least 90%, 91%, 92%, 93%, 94%, 95%, 96%, 97%, 98%, or 99% identical to, SEQ ID NO:8. A variant cellodextrin phosphorylase enzyme (e.g., between 90-99% amino acid identity with SEQ ID NO:2, 4, 6, or 8 reference sequence) should have some of (e.g., at least 30%, 40%, 50%, 60%, 70%, 80%, or 90% of), or all of, the enzymatic activity (refer to above definitions) of the corresponding non-variant reference sequence. Production of cellulose using a cellodextrin phosphorylase enzyme can be accomplished with an enzymatic reaction as disclosed herein, for example.

Cellulose as produced by a cellodextrin phosphorylase enzyme of the present disclosure can have a cellulose II crystal structure; such cellulose has not been subjected to a mercerization or derivatization process. Cellulose herein as it exists immediately or shortly after (e.g., less than about 0.5, 1, 5, 10, 15, 30, 60, 90, or 120 minutes) its enzymatic synthesis by a cellodextrin phosphorylase enzyme can comprise cellulose in the cellulose II crystal state. In contrast to cellulose as presently disclosed, cellulose produced in nature (e.g., in plants) typically is of a cellulose I structure and generally requires mercerization and/or other chemical treatments (e.g., derivatization followed by un-derivatization, formation of regenerated cellulose) to convert it into cellulose II. Cellulose in certain embodiments herein comprises cellulose in the cellulose II crystal state under both aqueous and dry conditions.

Cellulose of a composition as presently disclosed is insoluble in aqueous solvents such as water. In contrast, it can be soluble in certain non-aqueous solvents such as those comprising dimethyl sulfoxide (DMSO) and/or N,N-dimethylacetamide (DMAc). Examples of such solvents include DMSO or DMAc alone or further comprising lithium chloride (LiCl) (e.g., DMSO/LiCl and DMAc/LiCl). A DMSO/LiCl solvent or DMSO/LiCl solvent herein can comprise about 0.5, 1, 2, 3, 4, 5, 6, 7, 8, 9, or 10 wt % LiCl, for example, or can be LiCl-saturated. The concentration of cellulose herein can be at about 0.1-30 wt %, 0.1-20 wt %, 0.1-10 wt %, or 0.1-5 wt %, for example, or can be at about, or at least about, 0.1, 0.3, 0.5, 1, 2, 3, 4, 5, 6, 7, 8, 9, 10, 15, 20, 25, or 30 wt % in a non-aqueous solvent such as one comprising DMSO and/or DMAc. DMSO- and DMAc-comprising solvents herein do not further comprise an acid in certain aspects. Cellulose herein can be dissolved in any of the foregoing DMSO- and DMAc-based solvents at a relatively low temperature, such as at 15-30° C., 20-30° C., or 20-25° C. (e.g., room temperature), for example. In preferred embodiments, heat does not need to be applied to dissolve the cellulose.

A composition comprising a cellulose herein can be non-aqueous (e.g., a dry composition). Examples of such embodiments include films/coatings, powders, granules, microcapsules, flakes, or any other form of particulate matter. Other examples include larger compositions such as pellets, bars, kernels, beads, tablets, sticks, or other agglomerates. A non-aqueous or dry composition herein typically has less than 3, 2, 1, 0.5, or 0.1 wt % water comprised therein. The amount of cellulose herein in a non-aqueous or dry composition can be about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, or 99.9 wt %, for example.

In certain embodiments of the present disclosure, a composition comprising cellulose can be an aqueous composition that optionally has a viscosity of at least about 100 cPs. An aqueous composition herein can have a viscosity of at least about 100, 250, 500, 750, 1000, 2000, 3000, 4000, 5000, 6000, 7000, 8000, 9000, 10000, 11000, 12000, 13000, 14000, 15000, 16000, 17000, 18000, 19000, 20000, 25000, 30000, 35000, 40000, 45000, or 50000 cPs (or any integer between 100 and 50000 cPs), for example. Examples of aqueous compositions herein include colloidal dispersions.

Viscosity can be measured with an aqueous composition herein at any temperature between about 3° C. to about 110° C. (or any integer between 3 and 110° C.), for example. Alternatively, viscosity can be measured at a temperature between about 4° C. to 30° C., or about 20° C. to 25° C., for instance. Viscosity can be measured at atmospheric pressure (about 760 torr) or any other higher or lower pressure.

The viscosity of an aqueous composition disclosed herein can be measured using a viscometer or rheometer, or using any other means known in the art. It would be understood by those skilled in the art that a viscometer or rheometer can be used to measure the viscosity of aqueous compositions herein that exhibit shear thinning behavior (i.e., having viscosities that vary with flow conditions). The viscosity of such embodiments can be measured at a rotational shear rate of about 0.1 to 1000 rpm (revolutions per minute), for example. In some embodiments, viscosity can be measured at a rotational shear rate of about 10, 60, 150, 250, or 600 rpm.

The pH of an aqueous composition disclosed herein can be between about 2.0 to about 12.0, for example. Alternatively, pH can be about 2.0, 3.0, 4.0, 5.0, 6.0, 7.0, 8.0, 9.0, 10.0, 11.0, 12.0; or between 5.0 to about 12.0; or between about 4.0 and 8.0; or between about 5.0 and 8.0, for example.

An aqueous composition herein can comprise a solvent having at least about 10 or 20 wt % water. In other embodiments, a solvent comprises at least about 30, 40, 50, 60, 70, 80, 90, or 100 wt % water (or any integer value between 10 and 100 wt %), for example.

Cellulose of the present disclosure can be present as insoluble material in an aqueous composition at a wt % of about, or at least about, 0.01, 0.05, 0.1, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 wt %, for example. Example 4 below demonstrates that cellulose in certain aspects provides high viscosity to aqueous compositions at relatively low concentrations of the cellulose. Thus, certain embodiments of the present disclosure are drawn to aqueous compositions with less than about 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0.5 wt % cellulose herein.

An aqueous composition herein can comprise other components in addition to the disclosed cellulose. For example, the aqueous composition can comprise one or more salts such as a sodium salt (e.g., NaCl, $Na_2SO_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in an aqueous composition, for example. A salt can be present in an aqueous composition herein at a wt % of about (or at least about) 0.01 to about 10.00 (or any hundredth increment between 0.01 and 10.00), for example.

An aqueous composition comprising cellulose herein can be a colloidal dispersion, for example. The average size/diameter of cellulose particles in a colloidal dispersion herein typically ranges from between about 1 nm to 200000 nm (200 micrometers). Average particle size can be about 1-100 nm, 1-1000 nm, 1-10000 nm, 1-100000 nm, 1-200000 nm, 10-100 nm, 10-1000 nm, 10-10000 nm, 10-100000 nm, 10-200000 nm, 100-1000 nm, 100-10000 nm, 100-100000 nm, 100-200000 nm, 1000-10000 nm, 1000-100000, 1000-200000 nm, 10000-100000 nm, or 10000-200000 nm in some examples.

Aqueous compositions in certain embodiments have shear thinning behavior. Shear thinning behavior is observed as a decrease in viscosity of an aqueous composition as shear rate increases. Modification of the shear thinning behavior of an aqueous composition can be due to the admixture of cellulose herein to the aqueous composition. Thus, one or more cellulose materials of the present disclosure can be added to an aqueous composition to modify its rheological profile (i.e., the flow properties of an aqueous liquid, solution, or mixture are modified). Also, one or more cellulose materials herein can be added to an aqueous composition to modify its viscosity.

The rheological properties of aqueous compositions herein can be observed by measuring viscosity over an increasing rotational shear rate (e.g., from about 0.1 rpm to about 1000 rpm). For example, shear thinning behavior of an aqueous composition disclosed herein can be observed as a decrease in viscosity (cPs) by at least about 5%, 10%, 15%, 20%, 25%, 30%, 35%, 40%, 45%, 50%, 55%, 60%, 65%, 70%, 75%, 80%, 85%, 90%, or 95% (or any integer between 5% and 95%) as the rotational shear rate increases from about 10 rpm to 60 rpm, 10 rpm to 150 rpm, 10 rpm to 250 rpm, 60 rpm to 150 rpm, 60 rpm to 250 rpm, or 150 rpm to 250 rpm.

Non-limiting examples of compositions and methods disclosed herein include:

1. An enzymatic reaction comprising water, glucose-1-phosphate, cellodextrin, and a cellodextrin phosphorylase enzyme that synthesizes insoluble cellulose (e.g., a cellodextrin phosphorylase enzyme comprising an amino acid sequence that is at least 90% identical to SEQ ID NO:2 or SEQ ID NO:6, and that synthesizes insoluble cellulose).
2. The enzymatic reaction of embodiment 1, wherein the cellulose has a weight-average degree of polymerization ($DP_w$) of (i) about 10 to about 30, or (ii) about 10 to about 1000.
3. The enzymatic reaction of embodiment 1 or 2, wherein the cellodextrin comprises cellobiose.
4. A method for producing insoluble cellulose, the method comprising:
   a) contacting at least water, glucose-1-phosphate, cellodextrin, and a cellodextrin phosphorylase enzyme such as one comprising an amino acid sequence that is at least 90% identical to SEQ ID NO:2 or SEQ ID NO:6, wherein insoluble cellulose is produced; and
   b) optionally, isolating the insoluble cellulose produced in step (a).
5. The method of embodiment 4, wherein the cellulose produced in step (a) has a weight-average degree of polymerization ($DP_w$) of (i) about 10 to about 30, or (ii) about 10 to about 1000.
6. The method of embodiment 4 or 5, wherein the cellulose produced in step (a) has a cellulose II crystal structure.
7. The method of embodiment 4, 5, or 6, wherein the cellodextrin comprises cellobiose.
8. The method of embodiment 4, 5, 6, or 7, wherein the glucose-1-phosphate is provided in step (a) by providing a second reaction, wherein the products of the second reaction comprise glucose-1-phosphate.
9. The method of embodiment 8, wherein the second reaction produces glucose-1-phosphate by:
   (i) contacting water, inorganic phosphate, starch, a starch phosphorylase, and optionally a starch debranching enzyme such as a pullulanase or isoamylase;
   (ii) contacting water, inorganic phosphate, sucrose, and a sucrose phosphorylase enzyme; or
   (iii) contacting water, inorganic phosphate, cellulosic biomass, an endoglucanase, a cellodextrin phosphorylase, and optionally, a lytic polysaccharide monooxygenase and/or a cellobiohydrolase.
10. The method of embodiment 8 or 9, wherein the second reaction is provided in the same vessel in which step (a) is performed, and wherein the second reaction is performed before and/or continuously with step (a).

EXAMPLES

The present disclosure is further exemplified in the following Examples. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Example 1

Expression and Analysis of a *Vibrio ruber* Cellodextrin Phosphorylase

This Example describes expression of a putative *Vibrio ruber* cellodextrin phosphorylase enzyme in *E. coli*. Also, this Example demonstrates that this enzyme is indeed a cellodextrin phosphorylase through analysis of enzyme specific activity.

A putative cellodextrin phosphorylase, VruCdp1 (also referred to herein as "CRC03362-VruCdp1"), was identified in *Vibrio ruber* DSM14379. The nucleic acid sequence encoding VruCdp1 was predicted based on a genomic sequence, and is presented as SEQ ID NO:1. The amino acid sequence of VruCdp1 encoded by SEQ ID NO:1 is presented as SEQ ID NO:2.

Putative VruCdp1 cellodextrin phosphorylase was next heterologously expressed in *E. coli*, as follows. A polynucleotide sequence encoding VruCdp1 was codon-optimized for expression in *E. coli*. This sequence (SEQ ID NO:3) was inserted into the pET30a (Novagen) expression vector at the NdeI and XhoI sites by Generay (Shanghai, China), resulting in plasmid pZZH634. SEQ ID NO:3 contains the codon-optimized open reading frame as well as sequence encoding two extra amino acids (Leu-Glu) and a 6×His-tag at the C-terminus. The amino acid sequence encoded by SEQ ID NO:3 is presented as SEQ ID NO:4. The pZZH634 plasmid was transformed into *E. coli* strain BL21(DE3) (Novagen), which was plated on LB agar plates supplemented with 50 ppm kanamycin. Correctly transformed colonies, as confirmed by PCR and sequencing, were inoculated into 5 ml LB medium supplemented with 50 ppm kanamycin and cultivated in 37° C. with shaking for about 16 hours. About 1 mL of the culture was then inoculated into 25 mL LB medium supplemented with 50 ppm kanamycin and cultivated in 37° C. with shaking until the $OD_{600}$ reached about 0.4-1.0. IPTG was then added into the culture at a final concentration at 100 mM to induce VruCdp1 expression. The culture was then cultivated at 16° C. for 12-16 hours.

After this period of inducing VruCdp1 expression, the *E. coli* cells were pelleted, resuspended in lysis buffer (50 mM Tris pH 7.0, 500 mM NaCl, 10% glycerol, 0.1% Tween-20), and lysed on ice via ultra-sonication for 10 min (35% power, 20 min, 2 sec on/2 sec off) (SCIENT2-II D, Ningbo Scientz Biotechnology Co., Ltd). The lysate was cleared by centrifugation at 13000 rpm for 30 min (BECKMAN COULTER, Avanti™ JE). The clarified lysate was applied onto a His Trap™ HP (5 mL) (GE Healthcare) pre-equilibrated with 50 mM Tris pH 7.0, 500 mM NaCl, and 10% glycerol. The target protein (VruCdp1) was eluted from the column with a linear gradient from 0 to 250 mM imidazole in equilibration buffer. The fractions containing the target protein were pooled, concentrated and exchanged to equilibration buffer using 10K Amicon Ultra devices, and stored in 40% glycerol at −20° C. until usage.

The activity of VruCdp1 (isolated above) was measured using 10 mM G-1-P (Sigma G7000, α-D-Glucose 1-phosphate disodium salt hydrate) and 5 mM cellobiose (Sigma C7252, D-(+)-cellobiose) as substrates. The assay was performed in 25 mM Tris-HCl buffer, pH 7.0 at 37° C. for 10 minutes. Phosphorus release from the enzyme reaction was quantified using PiBlue™ reagent (BioAssay Systems, US).

One unit of cellodextrin phosphorylase activity was defined as the amount of enzyme that releases 1 µmol of inorganic phosphorus per minute under the assay conditions. The specific activity of the isolated VruCdp1 was determined to be 18.4 units/mg. Based on this observation, VruCdp1 was determined to be a cellodextrin phosphorylase (EC 2.4.1.49) belonging to glycosyl hydrolase family 94 (GH94, CAZy number).

Thus, an enzyme comprising SEQ ID NO:2 (VruCdp1) was expressed, isolated and shown to have cellodextrin phosphorylase activity.

Example 2

Expression and Analysis of a *Ruminococcus Champanellensis* Cellodextrin Phosphorylase This Example describes expression of a putative *Ruminococcus champanellensis* cellodextrin phosphorylase enzyme in *E. coli*. Also, this Example demonstrates that this enzyme is indeed a cellodextrin phosphorylase through analysis of enzyme specific activity.

A putative cellodextrin phosphorylase, RchCdp1 (also referred to herein as "CRC03359-RchCdp1"), was identified in *Ruminococcus* champanellensis 18P13. The nucleic acid sequence encoding RchCdp1 (positions 2373141 to 2375537 of GENBANK Accession No. NC_021039.1) is presented as SEQ ID NO:5. The amino acid sequence of RchCdp1 encoded by SEQ ID NO:5 is presented as SEQ ID NO:6.

Putative RchCdp1 cellodextrin phosphorylase was next heterologously expressed in *E. coli*, as follows. A polynucleotide sequence encoding RchCdp1 was codon-optimized for expression in *E. coli*. This sequence (SEQ ID NO:7) was inserted into the pET30a (Novagen) expression vector at the NdeI and XhoI sites by Generay (Shanghai, China), resulting in plasmid pZZH631. SEQ ID NO:7 contains the codon-optimized open reading frame as well as sequence encoding two extra amino acids (Leu-Glu) and a 6×His-tag at the C-terminus. The amino acid sequence encoded by SEQ ID NO:7 is presented as SEQ ID NO:8. The pZZH631 plasmid was transformed into *E. coli* strain BL21(DE3) (Novagen), which was plated on LB agar plates supplemented with 50 ppm kanamycin. Correctly transformed colonies, as confirmed by PCR and sequencing, were inoculated into 5 ml LB medium supplemented with 50 ppm kanamycin and cultivated in 37° C. with shaking for about 16 hours. About 1 mL of the culture was then inoculated into 25 mL LB medium supplemented with 50 ppm kanamycin and cultivated in 37° C. with shaking until the $OD_{600}$ reached about 0.4-1.0. IPTG was then added into the culture at a final concentration at 100 mM to induce RchCdp1 expression. The culture was then cultivated at 16° C. for 12-16 hours.

After this period of inducing RchCdp1 expression, the *E. coli* cells were pelleted, resuspended in lysis buffer (50 mM Tris pH 7.0, 500 mM NaCl, 10% glycerol, 0.1% Tween-20), and lysed on ice via ultra-sonication for 10 min (35% power, 20 min, 2 sec on/2 sec off) (SCIENT2-II D, Ningbo Scientz Biotechnology Co., Ltd). The lysate was cleared by centrifugation at 13000 rpm for 30 min (BECKMAN COULTER, Avanti™ JE). The clarified lysate was applied onto a His Trap™ HP (5 mL) (GE Healthcare) pre-equilibrated with 50 mM Tris pH 7.0, 500 mM NaCl, and 10% glycerol. The target protein (RchCdp1) was eluted from the column with a linear gradient from 0 to 250 mM imidazole in equilibration buffer. The fractions containing the target protein were pooled, concentrated and exchanged to equilibration buffer using 10K Amicon Ultra devices, and stored in 40% glycerol at −20° C. until usage.

The activity of RchCdp1 (isolated above) was measured using 10 mM G-1-P (Sigma G7000, α-D-Glucose 1-phosphate disodium salt hydrate) and 5 mM cellobiose (Sigma C7252, D-(+)-cellobiose) as substrates. The assay was performed in 25 mM Tris-HCl buffer, pH 7.0 at 37° C. for 10 minutes. Phosphorus release from the enzyme reaction was quantified using PiBlue™ reagent (BioAssay Systems, US). One unit of cellodextrin phosphorylase activity was defined as the amount of enzyme that releases 1 µmol of inorganic phosphorus per minute under the assay conditions. The specific activity of the isolated RchCdp1 was determined to be 15.4 units/mg. Based on this observation, RchCdp1 was determined to be a cellodextrin phosphorylase (EC 2.4.1.49) belonging to glycosyl hydrolase family 94 (GH94, CAZy number).

Thus, an enzyme comprising SEQ ID NO:6 (RchCdp1) was expressed, isolated and shown to have cellodextrin phosphorylase activity.

Example 3

Using *V. ruber* and *R. champanellensis* Cellodextrin Phosphorylases to Produce Low Molecular Weight, Insoluble Cellulose This Example describes using the cellodextrin phosphorylases described in Examples 1 and 2 to produce cellulose when applied in reactions containing G-1-P and cellodextrin.

A reaction comprising G-1-P and cellobiose in the presence of a *V. ruber* cellodextrin phosphorylase (VruCdp1, refer to Example 1) produced insoluble polysaccharide. To generate enough insoluble polysaccharide for analysis, a scale-up reaction was conducted by adding 1 g G-1-P, 0.25 g cellobiose, and 400 µg (~7.4 units) isolated VruCdp1 to a glass bottle containing 80 mL of 25 mM Tris buffer pH 7.0. The reaction was incubated overnight at 37° C. Insoluble polysaccharide product was collected by centrifugation at 3000 rpm for 20 minutes. This material was determined to be low molecular weight cellulose (refer to Example 4 below).

A reaction comprising G-1-P and cellobiose in the presence of an *R. champanellensis* cellodextrin phosphorylase (RchCdp1, refer to Example 2) produced insoluble polysaccharide. To generate enough insoluble polysaccharide for analysis, a scale-up reaction was conducted by adding 1 g G-1-P, 0.25 g cellobiose, and 400 µg (~6.2 units) isolated RchCdp1 to a glass bottle containing 80 mL of 25 mM Tris buffer pH 7.0. The reaction was incubated overnight at 37° C. Insoluble polysaccharide product was collected by centrifugation at 3000 rpm for 20 minutes. This material was determined to be low molecular weight cellulose (refer to Example 4 below).

Thus, enzymes comprising SEQ ID NO:2 (VruCdp1) or SEQ ID NO:6 (RchCdp1) produce low molecular weight, insoluble cellulose when provided in a reaction comprising G-1-P and cellodextrin (e.g., cellobiose) substrates. It is noteworthy that these enzymes had this particular cellulose synthesis activity, given that sixteen other cellodextrin phosphorylases that were similarly expressed and analyzed did not have this capability (data not shown).

Example 4

Analysis of Insoluble Polysaccharides Produced by *V. ruber* and *R. Champanellensis* Cellodextrin Phosphorylases This Example describes various analyses of the insoluble polysaccharide products obtained in the reactions described in Example 3. These analyses indicate that the products comprise low molecular weight, insoluble cellulose.

$^1$H-NMR analysis was conducted on the insoluble materials produced by *V. ruber* and *R. champanellensis* cellodextrin phosphorylases (Example 3). Briefly, 13.8 mg of each sample was dissolved by stirring in 0.8 ml of DMSO-d6, 3 wt % LiCl for 1 hour at 60° C. NMR was run on the dissolved samples using an AVANCE III HD NMR device equipped with a 5-mm CPC Q1 cryoprobe. This analysis indicated that the insoluble materials are polymers of glucose with beta-1,4 linkage, which is the characteristic linkage of cellulose. Thus, the insoluble materials produced by *V. ruber* and *R. champanellensis* cellodextrin phosphorylases comprise insoluble cellulose.

Each insoluble cellulose material was further analyzed using triple-detector SEC (size exclusion chromatography) to determine its molecular weight ($M_w$). Briefly, each sample was dissolved at 0.1-0.3 wt % in DMSO, 2 wt % LiCl and run through SEC. The $M_w$ for each sample was found to be about 3-4 kDa ($DP_w$~18-24) (Table 2).

TABLE 2

Molecular Weight of Cellulose Produced by RchCdp1 and VruCdp1 Enzymes

| Cellulose Product of: | Mn[a] (kDa) | Mp[b] (kDa) | Mw[c] (kDa) | Mz[d] (kDa) | DPw[e] | Calculated mass (µg) | IV[f] (mL/g) | Uncertainty in IV |
|---|---|---|---|---|---|---|---|---|
| RchCdp1 | 2.94 | 2.99 | 2.95 | 3 | 18.2 | 140.81 | 6.441 | 1.47% |
| VruCdp1 | 3.82 | 3.9 | 3.83 | 3.8 | 23.6 | 133.8 | 6.277 | 1.89% |

[a]Mn, number average molecular weight.
[b]Mp, peak molecular weight.
[c]Mw, mass average molecular weight.
[d]Mz, z-average molecular weight.
[e]DPw, mass average degree of polymerization.
[f]IV, intrinsic viscosity.

Thus, the cellulose samples produced by each of the RchCdp1 and VruCdp1 enzymes were of much lower molecular weight compared to cellulose obtained from cotton, wood pulp and microbial sources.

The low molecular weight cellulose samples were readily soluble and filterable in DMSO/LiCl (preparations as provided for SEC analysis above) and DMAc/LiCl (5 wt % LiCl in DMAc) at room temperature. This is noteworthy, since cellulose obtained from wood pulp, for example, typically cannot be dissolved in DMSO/LiCl, and requires elevated temperatures (e.g., about 100° C.) and times (e.g., 1 or more days) to dissolve in DMAc/LiCl. Since there was a clear viscometer peak observed with each of the samples (data not shown), it appears that enzymatically produced low molecular weight cellulose molecules behave as rigid rods.

Both as-made (produced as in Example 3 and stored in water, but never dried) and dried cellulose material (as synthesized by both RchCdp1 and VruCdp1 enzymes) exhibited a reflection indicative of cellulose II crystal under wide angle X-ray scattering (WAXS) analysis, which is the most stable crystal form of cellulose. It is noteworthy that, although the as-made samples were provided in an abundance of water after enzymatic production (98.5 wt % and 97.5 wt % water, respectively, for cellulose products of RchCdp1 and VruCdp1 enzymes), a clear reflection was still observed, superimposed to a broad amorphous diffraction from the water. This observation of cellulose II structure is interesting, since it is believed that cellulose II is typically obtained after cellulose has undergone certain chemical processing steps (e.g., mercerization; derivatization followed by recovery of non-derivatized cellulose) (Kroon-Batenburg and Kroon, Glycoconjugate J. 14:677-690). In contrast, the present Example demonstrates that cellulose as directly produced in reactions containing RchCdp1 and VruCdp1 enzymes has a cellulose II crystal structure, without application of any post-synthesis chemical treatments.

Atomic force microscopy (AFM) was used to analyze a thin film made from drying a colloidal dispersion of insoluble cellulose synthesized by either RchCdp1 or VruCdp1 enzymes. Briefly, a film was casted from a ~2 wt % dispersion of insoluble cellulose in water using a blade coater with a 3-mil thickness. The coated wet film was allowed to dry by slow water evaporation at room temperature. AFM analysis (FIGS. 1A and 1B) of dried coatings showed a unique morphology of sheets with a highly uniform thickness of about 5 nm and width of hundreds of nanometers. It is believed that such a two-dimensional, graphene-like cellulose coating has never previously been demonstrated. Typically rather, cellulose materials such as nano-crystalline cellulose and those from microbial sources form rod-like colloids, not two-dimensional flake-like structures. Flake-like two dimensional structures are contemplated to have a number of advantages. For example, cellulose material with such structural properties likely has enhanced oxygen- and/or water-barrier properties. Moreover, the highly crystalline nature of the cellulose materials provided herein should allow increased mechanical properties of traditional thermoplastic polymers.

The above-prepared colloidal dispersions of insoluble cellulose could easily be coated to yield highly transparent, continuous films. Such film had a very thin thickness ranging between 1 and 2 microns, with a roughness of about 300 nm (data not shown). Thus, the low molecular weight, insoluble cellulose material provided herein is contemplated to be useful in water-based coating systems that can enable a number of applications. Examples of such applications include oxygen- and water vapor-barrier coatings on packaging plastics, as well as edible coating on fruits and vegetables to increase product shelf life. Moreover, the disclosed coatings can be useful for seed coating applications and for enabling active ingredient release in pharmaceutical compositions.

Colloidal dispersions in water containing 1.7-2.5 wt % of insoluble cellulose synthesized by either RchCdp1 or VruCdp1 enzymes were analyzed for their degree of viscosity. Briefly, a Brookfield rheometer was used to obtain viscosity versus shear rate data, where the viscosity was measured at 10 (1/s) shear rate from the curves. It was found that both colloidal dispersions exhibit high viscosity that was 10000 times higher than the viscosity of water (FIG. 2). Also, the dispersions exhibited shear thinning behavior (where viscosity decreases as a function of shear rate), which is desired in many thickening applications. It is noteworthy to have obtained such high viscosity levels, given that each insoluble cellulose sample was of low DPw (less than 25 DPw, Table 2). In fact, commercially available carboxymethyl-derivatized cellulose (water-soluble) required significantly higher DPw (about 1000 or higher) to increase viscosity in water to the same extent as the viscosity observed when using the insoluble cellulose samples provided herein (FIG. 3).

Thus, the insoluble polysaccharide materials produced by *V. ruber* and *R. champanellensis* cellodextrin phosphorylases comprise low molecular weight, insoluble cellulose. This cellulose has a $DP_w$ of about 18-24 and exhibits a cellulose II crystal structure. The cellulose II crystal structure is not a result of chemical processing such as mercerization or derivatization/un-derivatization processes, but rather characterizes the insoluble cellulose material as it is directly produced enzymatically. The unique properties of the insoluble cellulose provided herein gives this material broad utility, such as use in viscosity- and rheology-modification applications, and film/barrier applications.

What is claimed is:

1. An isolated composition comprising:
   (i) insoluble cellulose having a weight-average degree of polymerization (DPw) of at least 15, and
   (ii) a cellodextrin phosphorylase enzyme comprising an amino acid sequence that is at least 90% identical to SEQ ID NO:2 or SEQ ID NO:6.

2. The isolated composition of claim 1, wherein the insoluble cellulose has a DPw of at least 17.

3. The isolated composition of claim 1, wherein the insoluble cellulose has a DPw of 15 to 50.

4. The isolated composition of claim 1, wherein the insoluble cellulose has a DPw of 15 to 30.

5. The isolated composition of claim 1, wherein the insoluble cellulose has a DPw of 17 to 50.

6. The isolated composition of claim 1, wherein the insoluble cellulose has a DPw of 17 to 30.

7. The isolated composition of claim 1, wherein the insoluble cellulose has a cellulose II crystal structure.

8. The isolated composition of claim 1, wherein the cellodextrin phosphorylase enzyme comprises an amino acid sequence that is at least 95% identical to SEQ ID NO:2 or SEQ ID NO:6.

9. The isolated composition of claim 2, wherein the cellodextrin phosphorylase enzyme comprises an amino acid sequence that is at least 95% identical to SEQ ID NO:2 or SEQ ID NO:6.

10. The isolated composition of claim 3, wherein the cellodextrin phosphorylase enzyme comprises an amino acid sequence that is at least 95% identical to SEQ ID NO:2 or SEQ ID NO:6.

11. The isolated composition of claim 4, wherein the cellodextrin phosphorylase enzyme comprises an amino acid sequence that is at least 95% identical to SEQ ID NO:2 or SEQ ID NO:6.

12. The isolated composition of claim 5, wherein the cellodextrin phosphorylase enzyme comprises an amino acid sequence that is at least 95% identical to SEQ ID NO:2 or SEQ ID NO:6.

13. The isolated composition of claim 6, wherein the cellodextrin phosphorylase enzyme comprises an amino acid sequence that is at least 95% identical to SEQ ID NO:2 or SEQ ID NO:6.

14. The isolated composition of claim 1, wherein the cellodextrin phosphorylase enzyme is a *Vibrio* species cellodextrin phosphorylase enzyme or a *Ruminococcus* species cellodextrin phosphorylase enzyme.

* * * * *

SEQUENCE LISTING

```
<160> NUMBER OF SEQ ID NOS: 8

<210> SEQ ID NO 1
<211> LENGTH: 2415
<212> TYPE: DNA
<213> ORGANISM: Vibrio ruber
<220> FEATURE:
<221> NAME/KEY: misc_feature
<222> LOCATION: (1)..(2415)
<223> OTHER INFORMATION: VruCdp1_wild type

<400> SEQUENCE: 1
atgatgaaat tcggatattt tgacgataaa aataaagaat atgttgccac aacaccatgt      60
acaccaatca aatggtgtaa ttatgtggga actttaaact ttggtggttt agtcgatagt     120
aacggcggta ttttactgtg taagggtgat cccgcactca atcgtatcac caaatatatt     180
gcccagatgc ccaatgccga ctttaaaggt tcgacactct atttgaaggt tcgcaatcaa     240
aacggggaag tgacaatatt ttctccgttt tatacaccga ctttaaagcc gttagataaa     300
tttgaaaatc acaccggact ttcttatacc accattattg ccgaagctta tggtgtgcgc     360
tgtgagagca ctttctttgt accgaagcag gacccgtttt tactgcaaga tattaaagtg     420
accaatattt ccggtgagga tttacatgtt gatgtgatac ccgtggttga attcaccac      480 tttgatgcat tgaagcaatt ggtgaatgcc gactgggtgc ctcagaccat gattttgcaa     540
gcacatcatc aagatttggg acataccgtt ttggaacagt atgcctttat gaagcgtgat     600
tatgctgtga acttactgac cgctgatcgg ccagcgactt catttgacgg ggatcgccag     660
aagttccttg gtaacctcgg gtatggcagt tgggcggcac cggcagcact caatgatgca     720
gaactgacca acagcgagtg tttgcgcggc gataatatcg gtgcgctgaa cttacgttta     780
ggctggctga aacctcagca aaccgagcgg acggtggtgc agttgactca gatggcgagt     840
ctcgatgcgg cacaaccgat gttagagaaa tatcgcgatc atcaagtggt tgatcaggct     900
tttgccgcac tgggcgagtt ctgggatgac tatttatcgg cgattcaagt ggctacacct     960
gatgcagcaa tgaactcaat gctgaatgtg cacaacccgc gtcagtgtca caccaccaaa    1020
aactggtcgc gttatttatc actgtatcag ctcggctatg gtgcgcgtgg gatcgggttc    1080
cgcgattcat cgcaggatat tctcggtgtg atcagccaca tgcctgaaga agcacgcgaa    1140
tttatcgaac gtttgctgtc agtgcaaaat accgatggtt ccgctatgca tcagttcttc    1200
ccttcaacca tggaagccaa tgccggtgac tcacgtgaag aagaagaccg ccctgactac    1260
tatggtgatg atcacttgtg gatcatttat gccgtcacgc aatatgtgaa agaaaccggt    1320
aatgcagatt ttctcaacca agtgattcct tattatcaaa aagataaaca gggtaatccg    1380
gttgagtcag ggacggtttg ggatcattta tgccgggcga ttgattttac ggcaacgcat    1440
accgggcagc atggcttacc gttgctggga ttcgcggact ggaatgacac agtgaactta    1500
ccgacgggtg ctgagtcgct gatggtcgcc aatatgtacg gtaaagcatt attggatatg    1560
```

-continued

```
ctcgatttgt gtcagctccg tggtgaggat tcgctcgcac agcgttacca aagccagtac    1620
gaacagatgc agcataccgt caatcagtat ggctgggacg gggaatggtt tgtccgttac    1680
tttgatgaaa aggggggcacc gattggttca cataccaatg ctcagggggca aatttatacc   1740 aatggacaaa gctggccggt gatctccggg tttgccacgc ctgagcgcgc catgcaagct    1800
ttggattctg ttcataccaa actcaatacc gcgaacggca ttaagctttc cactcccgga    1860
tataacggat tttcgcctga actgggcggg gtttctactt acccgcccgg agcgaaagag    1920
aatggcggga tcttcttgca cgcgaaccca tggatgatga ttgctgaaac caaagtcggc    1980
aatggtgatc gcgcttatca gtattaccga caaattaatc cggcttctaa gaatgatcag    2040
atcgaggtgt ttgagtctga accctactgt tatccgcaaa atattttggg agatgagcac    2100
ccgcaatttg gtttaggccg taatgcatgg ttgtccggta cgtcatcgtg gacatatgtg    2160
gcaggcacgc agtggatttt aggtgtgcgg cctgaagttg acgggttacg cattgatcct    2220
tgtattccgc gtgactggcc tgaattttcc gtacagcgga aattccgggg agcgacttac    2280
cggattcatg ttgccaatcc gcatcatgtc aaccggggcg tcacagagat gcgcgtcgat    2340
ggggttgtga tccaagggaa taaagcaccg gtatttaccg atggtgaaca tcatatcgag    2400
attactttag gtcaa                                                     2415
```

<210> SEQ ID NO 2
<211> LENGTH: 805
<212> TYPE: PRT
<213> ORGANISM: Vibrio ruber
<220> FEATURE:
<221> NAME/KEY: MISC_FEATURE
<222> LOCATION: (1)..(805)
<223> OTHER INFORMATION: VruCdp1_wild type protein

<400> SEQUENCE: 2

```
Met Met Lys Phe Gly Tyr Phe Asp Asp Lys Asn Lys Glu Tyr Val Ala
1               5                   10                  15

Thr Thr Pro Cys Thr Pro Ile Lys Trp Cys Asn Tyr Val Gly Thr Leu
            20                  25                  30

Asn Phe Gly Gly Leu Val Asp Ser Asn Gly Gly Ile Leu Leu Cys Lys
        35                  40                  45

Gly Asp Pro Ala Leu Asn Arg Ile Thr Lys Tyr Ile Ala Gln Met Pro
    50                  55                  60

Asn Ala Asp Phe Lys Gly Ser Thr Leu Tyr Leu Lys Val Arg Asn Gln
65                  70                  75                  80

Asn Gly Glu Val Thr Ile Phe Ser Pro Phe Tyr Thr Pro Thr Leu Lys
                85                  90                  95

Pro Leu Asp Lys Phe Glu Asn His Thr Gly Leu Ser Tyr Thr Thr Ile
            100                 105                 110

Ile Ala Glu Ala Tyr Gly Val Arg Cys Glu Ser Thr Phe Phe Val Pro
        115                 120                 125

Lys Gln Asp Pro Phe Leu Leu Gln Asp Ile Lys Val Thr Asn Ile Ser
    130                 135                 140

Gly Glu Asp Leu His Val Asp Val Ile Pro Val Val Glu Phe Thr His
145                 150                 155                 160

Phe Asp Ala Leu Lys Gln Leu Val Asn Ala Asp Trp Val Pro Gln Thr
                165                 170                 175

Met Ile Leu Gln Ala His His Gln Asp Leu Gly His Thr Val Leu Glu
            180                 185                 190
```

```
Gln Tyr Ala Phe Met Lys Arg Asp Tyr Ala Val Asn Leu Leu Thr Ala
            195                 200                 205

Asp Arg Pro Ala Thr Ser Phe Asp Gly Asp Arg Gln Lys Phe Leu Gly
210                 215                 220

Asn Leu Gly Tyr Gly Ser Trp Ala Ala Pro Ala Ala Leu Asn Asp Ala
225                 230                 235                 240

Glu Leu Thr Asn Ser Glu Cys Leu Arg Gly Asp Asn Ile Gly Ala Leu
                245                 250                 255

Asn Leu Arg Leu Gly Trp Leu Lys Pro Gln Thr Glu Arg Thr Val
            260                 265                 270

Val Gln Leu Thr Gln Met Ala Ser Leu Asp Ala Ala Gln Pro Met Leu
            275                 280                 285

Glu Lys Tyr Arg Asp His Gln Val Val Asp Gln Ala Phe Ala Ala Leu
            290                 295                 300

Gly Glu Phe Trp Asp Asp Tyr Leu Ser Ala Ile Gln Val Ala Thr Pro
305                 310                 315                 320

Asp Ala Ala Met Asn Ser Met Leu Asn Val His Asn Pro Arg Gln Cys
                325                 330                 335

His Thr Thr Lys Asn Trp Ser Arg Tyr Leu Ser Leu Tyr Gln Leu Gly
            340                 345                 350

Tyr Gly Ala Arg Gly Ile Gly Phe Arg Asp Ser Ser Gln Asp Ile Leu
            355                 360                 365

Gly Val Ile Ser His Met Pro Glu Glu Ala Arg Glu Phe Ile Glu Arg
            370                 375                 380

Leu Leu Ser Val Gln Asn Thr Asp Gly Ser Ala Met His Gln Phe Phe
385                 390                 395                 400

Pro Ser Thr Met Glu Ala Asn Ala Gly Asp Ser Arg Glu Glu Glu Asp
                405                 410                 415

Arg Pro Asp Tyr Tyr Gly Asp His Leu Trp Ile Ile Tyr Ala Val
            420                 425                 430

Thr Gln Tyr Val Lys Glu Thr Gly Asn Ala Asp Phe Leu Asn Gln Val
            435                 440                 445

Ile Pro Tyr Tyr Gln Lys Asp Lys Gln Gly Asn Pro Val Glu Ser Gly
450                 455                 460

Thr Val Trp Asp His Leu Cys Arg Ala Ile Asp Phe Thr Ala Thr His
465                 470                 475                 480

Thr Gly Gln His Gly Leu Pro Leu Leu Gly Phe Ala Asp Trp Asn Asp
                485                 490                 495

Thr Val Asn Leu Pro Thr Gly Ala Glu Ser Leu Met Val Ala Asn Met
            500                 505                 510

Tyr Gly Lys Ala Leu Leu Asp Met Leu Asp Leu Cys Gln Leu Arg Gly
            515                 520                 525

Glu Asp Ser Leu Ala Gln Arg Tyr Gln Ser Gln Tyr Glu Gln Met Gln
530                 535                 540

His Thr Val Asn Gln Tyr Gly Trp Asp Gly Glu Trp Phe Val Arg Tyr
545                 550                 555                 560

Phe Asp Glu Lys Gly Ala Pro Ile Gly Ser His Thr Asn Ala Gln Gly
                565                 570                 575

Gln Ile Tyr Thr Asn Gly Gln Ser Trp Pro Val Ile Ser Gly Phe Ala
            580                 585                 590

Thr Pro Glu Arg Ala Met Gln Ala Leu Asp Ser Val His Thr Lys Leu
            595                 600                 605

Asn Thr Ala Asn Gly Ile Lys Leu Ser Thr Pro Gly Tyr Asn Gly Phe
```

```
              610                 615                 620
Ser Pro Glu Leu Gly Gly Val Ser Thr Tyr Pro Pro Gly Ala Lys Glu
625                 630                 635                 640

Asn Gly Gly Ile Phe Leu His Ala Asn Pro Trp Met Met Ile Ala Glu
                645                 650                 655

Thr Lys Val Gly Asn Gly Asp Arg Ala Tyr Gln Tyr Tyr Arg Gln Ile
                660                 665                 670

Asn Pro Ala Ser Lys Asn Asp Gln Ile Glu Val Phe Glu Ser Glu Pro
            675                 680                 685

Tyr Cys Tyr Pro Gln Asn Ile Leu Gly Asp Glu His Pro Gln Phe Gly
            690                 695                 700

Leu Gly Arg Asn Ala Trp Leu Ser Gly Thr Ser Ser Trp Thr Tyr Val
705                 710                 715                 720

Ala Gly Thr Gln Trp Ile Leu Gly Val Arg Pro Glu Val Asp Gly Leu
                725                 730                 735

Arg Ile Asp Pro Cys Ile Pro Arg Asp Trp Pro Glu Phe Ser Val Gln
                740                 745                 750

Arg Lys Phe Arg Gly Ala Thr Tyr Arg Ile His Val Ala Asn Pro His
            755                 760                 765

His Val Asn Arg Gly Val Thr Glu Met Arg Val Asp Gly Val Val Ile
            770                 775                 780

Gln Gly Asn Lys Ala Pro Val Phe Thr Asp Gly Glu His His Ile Glu
785                 790                 795                 800

Ile Thr Leu Gly Gln
                805

<210> SEQ ID NO 3
<211> LENGTH: 2442
<212> TYPE: DNA
<213> ORGANISM: Artificial sequence
<220> FEATURE:
<223> OTHER INFORMATION: VruCdp1 with added sequences

<400> SEQUENCE: 3
atgatgaaat tcggctactt cgacgacaaa aacaaagaat atgttgcaac caccccgtgt      60
accccgatta atggtgtaa ttatgttggc accctgaatt ttggtggtct ggttgatagc     120
aatggtggta ttctgctgtg taaaggtgat ccggcactga tcgtattac aaatatatc     180 gcacagatgc cgaacgccga ttttaaaggt agcaccctgt atctgaaagt gcgtaatcag     240
aatggtgaag tgaccatttt tagcccgttt tatacccccga ccctgaaacc gctggataaa     300
tttgaaaatc ataccggtct gagctacacc accattattg ccgaagccta tggtgttcgt     360
tgtgaaagca cctttttttgt tccgaaacag gatccatttc tgctgcagga tatcaaagtt     420
accaatatca gcggtgaaga tctgcatgtt gatgttattc cggttgtgga atttacccat     480
tttgatgcac tgaaacagct ggttaatgca gattgggttc gcagaccat gattctgcag     540 gcacatcatc aggatctggg tcataccgtt ctggaacagt atgcatttat gaaacgtgat     600
tatgccgtta atctgctgac cgcagatcgt ccggcaacca gctttgatgg tgatcgtcag     660
aaattcctgg gtaatctggg ttatggtagc tgggcagcac cggcagcact gaatgatgca     720
gaactgacca atagcgaatg tctgcgtggt gataatattg gtgccctgaa tctgcgtctg     780
ggttggctga acctcagca gaccgaacgt accgttgttc agctgacaca gatggcaagc     840
ctggatgcag cacagccgat gctggaaaaa atcgtgatc atcaggttgt tgatcaggca     900
tttgcagcac tgggcgaatt tgggatgat tatctgagcg caattcaggt tgcgacaccg     960
```

```
gatgcagcca tgaatagcat gctgaatgtt cataatccgc gtcagtgtca taccacaaaa    1020
aattggagcc gttatctgag tctgtatcag ctgggctatg gtgcacgtgg tattggtttt    1080
cgtgatagca gccaggatat tctgggtgtt attagccaca tgccggaaga agcacgcgaa    1140
tttattgaac gtctgctgtc agttcagaat accgatggta gcgcaatgca tcagtttttt    1200
ccgagcacaa tggaagcaaa tgccggtgat agccgtgaag aagaagatcg tcctgattat    1260
tatggtgatg accatctgtg gattatctat gcagttaccc agtatgttaa agaaaccggc    1320
aatgccgatt ttctgaatca ggttattccg tactaccaga agataaaca gggtaatccg    1380 gttgaaagcg gcaccgtttg ggatcatctg tgccgtgcaa ttgatttcac cgcaacccat    1440
acaggtcagc atggcctgcc gctgctgggt tttgccgatt ggaatgatac cgtgaatctg    1500
ccgacaggtg cagaaagcct gatggttgcc aatatgtatg gtaaagcact gctggatatg    1560
ctggatctgt gccaactgcg tggcgaagat agcctggcac agcgttatca gagccagtat    1620
gagcagatgc agcataccgt taatcagtat ggttgggatg gtgaatggtt tgtgcgttat    1680
tttgatgaaa aaggcgcacc gattggtagc cataccaatg cacagggtca gatttatacc    1740
aatggtcaga gctggccagt tattagcggt tttgcaacac cggaacgtgc aatgcaggca    1800
ctggatagcg ttcataccaa actgaatacc gccaatggta ttaaactgag cacaccgggt    1860
tataatggtt ttagtccgga actgggtggt gttagcacct atccgcctgg tgcaaaagaa    1920
aatggtggca ttttctgca tgcaaatccg tggatgatga ttgcagaaac caaagttggt    1980
aatggcgatc gtgcatatca gtattatcgt cagattaatc cggcaagcaa aaacgatcag    2040
atcgaagttt ttgaaagcga gccgtattgt tatccgcaga catcctggg tgatgaacat    2100 ccgcagtttg gtctgggtcg taatgcatgg ctgagcggca ccagcagctg gacctatgtt    2160
gcaggcaccc agtggattct gggcgttcgt ccggaagttg atggcctgcg tattgatccg    2220
tgtattccgc gtgattggcc tgaatttagc gttcagcgta aatttcgtgg tgcaacctat    2280
cgtattcatg ttgccaatcc gcatcatgtt aatcgtggtg ttaccgaaat gcgtgttgat    2340
ggtgttgtta ttcagggtaa taaagcaccg gttttaccg atggcgaaca tcacattgaa    2400
attaccctgg gtcagctcga gcaccaccac caccaccact ga    2442
```

<210> SEQ ID NO 4
<211> LENGTH: 813
<212> TYPE: PRT
<213> ORGANISM: Artificial sequence
<220> FEATURE:
<223> OTHER INFORMATION: VruCdp1 with added sequences_protein

<400> SEQUENCE: 4

```
Met Met Lys Phe Gly Tyr Phe Asp Asp Lys Asn Lys Glu Tyr Val Ala
1               5                   10                  15

Thr Thr Pro Cys Thr Pro Ile Lys Trp Cys Asn Tyr Val Gly Thr Leu
                20                  25                  30

Asn Phe Gly Gly Leu Val Asp Ser Asn Gly Gly Ile Leu Leu Cys Lys
            35                  40                  45

Gly Asp Pro Ala Leu Asn Arg Ile Thr Lys Tyr Ile Ala Gln Met Pro
        50                  55                  60

Asn Ala Asp Phe Lys Gly Ser Thr Leu Tyr Leu Lys Val Arg Asn Gln
65                  70                  75                  80

Asn Gly Glu Val Thr Ile Phe Ser Pro Phe Tyr Thr Pro Thr Leu Lys
                85                  90                  95
```

-continued

```
Pro Leu Asp Lys Phe Glu Asn His Thr Gly Leu Ser Tyr Thr Thr Ile
            100                 105                 110
Ile Ala Glu Ala Tyr Gly Val Arg Cys Glu Ser Thr Phe Phe Val Pro
            115                 120                 125
Lys Gln Asp Pro Phe Leu Leu Gln Asp Ile Lys Val Thr Asn Ile Ser
        130                 135                 140
Gly Glu Asp Leu His Val Asp Val Ile Pro Val Val Glu Phe Thr His
145                 150                 155                 160
Phe Asp Ala Leu Lys Gln Leu Val Asn Ala Asp Trp Val Pro Gln Thr
                165                 170                 175
Met Ile Leu Gln Ala His His Gln Asp Leu Gly His Thr Val Leu Glu
            180                 185                 190
Gln Tyr Ala Phe Met Lys Arg Asp Tyr Ala Val Asn Leu Leu Thr Ala
        195                 200                 205
Asp Arg Pro Ala Thr Ser Phe Asp Gly Asp Arg Gln Lys Phe Leu Gly
    210                 215                 220
Asn Leu Gly Tyr Gly Ser Trp Ala Ala Pro Ala Ala Leu Asn Asp Ala
225                 230                 235                 240
Glu Leu Thr Asn Ser Glu Cys Leu Arg Gly Asp Asn Ile Gly Ala Leu
                245                 250                 255
Asn Leu Arg Leu Gly Trp Leu Lys Pro Gln Gln Thr Glu Arg Thr Val
            260                 265                 270
Val Gln Leu Thr Gln Met Ala Ser Leu Asp Ala Ala Gln Pro Met Leu
        275                 280                 285
Glu Lys Tyr Arg Asp His Gln Val Val Asp Gln Ala Phe Ala Ala Leu
    290                 295                 300
Gly Glu Phe Trp Asp Asp Tyr Leu Ser Ala Ile Gln Val Ala Thr Pro
305                 310                 315                 320
Asp Ala Ala Met Asn Ser Met Leu Asn Val His Asn Pro Arg Gln Cys
                325                 330                 335
His Thr Thr Lys Asn Trp Ser Arg Tyr Leu Ser Leu Tyr Gln Leu Gly
            340                 345                 350
Tyr Gly Ala Arg Gly Ile Gly Phe Arg Asp Ser Ser Gln Asp Ile Leu
        355                 360                 365
Gly Val Ile Ser His Met Pro Glu Glu Ala Arg Glu Phe Ile Glu Arg
    370                 375                 380
Leu Leu Ser Val Gln Asn Thr Asp Gly Ser Ala Met His Gln Phe Phe
385                 390                 395                 400
Pro Ser Thr Met Glu Ala Asn Ala Gly Asp Ser Arg Glu Glu Glu Asp
                405                 410                 415
Arg Pro Asp Tyr Tyr Gly Asp Asp His Leu Trp Ile Ile Tyr Ala Val
            420                 425                 430
Thr Gln Tyr Val Lys Glu Thr Gly Asn Ala Asp Phe Leu Asn Gln Val
        435                 440                 445
Ile Pro Tyr Tyr Gln Lys Asp Lys Gln Gly Asn Pro Val Glu Ser Gly
    450                 455                 460
Thr Val Trp Asp His Leu Cys Arg Ala Ile Asp Phe Thr Ala Thr His
465                 470                 475                 480
Thr Gly Gln His Gly Leu Pro Leu Leu Gly Phe Ala Asp Trp Asn Asp
                485                 490                 495
Thr Val Asn Leu Pro Thr Gly Ala Glu Ser Leu Met Val Ala Asn Met
            500                 505                 510
Tyr Gly Lys Ala Leu Leu Asp Met Leu Asp Leu Cys Gln Leu Arg Gly
```

```
            515                 520                 525
    Glu Asp Ser Leu Ala Gln Arg Tyr Gln Ser Gln Tyr Glu Gln Met Gln
        530                 535                 540

His Thr Val Asn Gln Tyr Gly Trp Asp Gly Glu Trp Phe Val Arg Tyr
    545                 550                 555                 560

Phe Asp Glu Lys Gly Ala Pro Ile Gly Ser His Thr Asn Ala Gln Gly
                    565                 570                 575

Gln Ile Tyr Thr Asn Gly Gln Ser Trp Pro Val Ile Ser Gly Phe Ala
                580                 585                 590

Thr Pro Glu Arg Ala Met Gln Ala Leu Asp Ser Val His Thr Lys Leu
                595                 600                 605

Asn Thr Ala Asn Gly Ile Lys Leu Ser Thr Pro Gly Tyr Asn Gly Phe
            610                 615                 620

Ser Pro Glu Leu Gly Gly Val Ser Thr Tyr Pro Pro Gly Ala Lys Glu
    625                 630                 635                 640

Asn Gly Gly Ile Phe Leu His Ala Asn Pro Trp Met Met Ile Ala Glu
                    645                 650                 655

Thr Lys Val Gly Asn Gly Asp Arg Ala Tyr Gln Tyr Tyr Arg Gln Ile
                660                 665                 670

Asn Pro Ala Ser Lys Asn Asp Gln Ile Glu Val Phe Glu Ser Glu Pro
                675                 680                 685

Tyr Cys Tyr Pro Gln Asn Ile Leu Gly Asp Glu His Pro Gln Phe Gly
            690                 695                 700

Leu Gly Arg Asn Ala Trp Leu Ser Gly Thr Ser Ser Trp Thr Tyr Val
    705                 710                 715                 720

Ala Gly Thr Gln Trp Ile Leu Gly Val Arg Pro Glu Val Asp Gly Leu
                    725                 730                 735

Arg Ile Asp Pro Cys Ile Pro Arg Asp Trp Pro Glu Phe Ser Val Gln
                740                 745                 750

Arg Lys Phe Arg Gly Ala Thr Tyr Arg Ile His Val Ala Asn Pro His
                755                 760                 765

His Val Asn Arg Gly Val Thr Glu Met Arg Val Asp Gly Val Val Ile
        770                 775                 780

Gln Gly Asn Lys Ala Pro Val Phe Thr Asp Gly Glu His Ile Glu
    785                 790                 795                 800

Ile Thr Leu Gly Gln Leu Glu His His His His His His
                    805                 810

<210> SEQ ID NO 5
<211> LENGTH: 2397
<212> TYPE: DNA
<213> ORGANISM: Ruminococcus champanellensis
<220> FEATURE:
<221> NAME/KEY: misc_feature
<222> LOCATION: (1)..(2397)
<223> OTHER INFORMATION: RchCdp1_wild type

<400> SEQUENCE: 5
atgcagtacg gttactttga ccttgcaaac aaggaatacg tcatcacaag acctgacacc      60
cctgctccct gggcaaacta cctgggagat ccggaatacg cgctatgat ctccaacaac      120 gcctgcggct acagctttgt aaagagcggc gcaaacggca gaatttcccg gttccggttc      180
aacagcaata tggcgctgcc cggcagatat atctacatcc gggacaatga cactgcggat      240
tactggtctg catcctggca gccggtgggc aagcccctgg atcagtacaa gagcgtatgc      300
cgccacggta ccgcttacac cattatgact gcggattatg caagcgtgca ttccgagacc      360
```

```
acctattatg tacoctatca ccagacctat gaggtttggc gcacaaagat caccaacacc    420
tccgacaagc ccagaaagct gtccgtgttc ggctttgtgg aattcaccaa cgacaacaac    480
tacgagcagg atcaggtaaa cctccagtac accctgttca tcacccgcac cagctttgag    540
gaaaaccgca tcatccagca catcaatgaa aacagcggca aggacgcttc cggctccaac    600
cacaaggagc gcttcttcgg catggtgggc gctccggttt ccggctggaa cggcaacctg    660
gacagcttca tcggccccta ccggacctat tccaacccca tcgccgtaga gcagggtaag    720
tgcgacggca gcatgaacta caactccaac gcatgcggcg ccctccagag cgacctggag    780
ctgacacccg gcgaaactgc agagctgatc tacattctcg gtcagcgcaa cagcgcagag    840
gctgctacca tcctggatac ctacaagacg ctgggcaagg tggatgcaga aatcgcagag    900
ctgaagaatt tctggcacaa ggagctgtcc aacttccagg tgaacacccc cagcccggaa    960
ttcaacaata tgatcaacgt atggaacgct taccagtgct tcatcacctt catctggtcc   1020
cgtgcggcat ccttcgtata ctgcggtctg cgcaacggct acggctatcg ggataccgtc   1080
caggatatcc agggcatcat tcacctggat ccggaaatgg cagcagacaa gatccgcttt   1140
atgctctccg cacaggttga caacggcggc ggtctgcccc tggtgaagtt caaccacaat   1200
gcgggtcatg agaacacccc ggacgatccg gagtatgtaa aggaaaccgg tcacccctcc   1260
taccgggcgg acgatgctct gtggctgttc cccaccattg tgaagtacat cggggaaagc   1320
ggcaacaagg cattcctgga cgaggtgatc gtatacgcca acggcggcga ggctacggta   1380
tacgaccacc tgaagaacgc tatccggttc tccatggagc ggctgggggc acacgatatg   1440
cctgccgggc tccatgcgga ctggaacgac tgtctgcgga tgggtgccaa gggtgagtcc   1500
acctttgtgg cattccagct gtactatgcg atgcgcgtga tccgggatat ggcacagcag   1560
cggggcgaca gcgattatgt agcttacatc gacgatatac aggcaaagct gggcgcatcc   1620
ctggaaaagt gctgggatgg ggatcggttc atccggggca tccgggaaga cggagtcgtt   1680
gtgggcgcaa agaaggatcc ggaagcctcc atgtggctca tccccagag ctgggcagtg   1740
atctccggct ttgcaagcaa ggatcaggca gagcagtcca tggaatccgt acaccggatt   1800
ctgaacaccc cctacggcat caagctgctg gatcctccct acagagcgca ttactttgac   1860
ggtgctctga tgcacatctt caatccggac accaaggaaa acggtggtat cttctcccag   1920
tcccagggct gggcgatcct ggcggaaagt ctgctgggtc acgaaaccg tgccttcgag   1980
tactttatgg aaagctcccc ggctgccatg aacgacaggg cggagatccg tgtcatggag   2040
ccgtatgtgc acggtcagtt caccgaaagc accgcttctc cctatgccgg ccgctcccat   2100
gtacactggc tcaccggtac cgcatccacc gttatggtag ctgcgtaga ggggatctgc   2160
ggcatgcgtc ccaatgcgga cggtctggtg atctctccct ccattccctc ctcctgggac   2220
ggcttcacca tcgagaaaaa cttccgtggc aagcatctgt ccatccgggt agagaatcct   2280
agccacgttc agagcggcgt caagtccctg accctcaacg gcaaggagct gtccggcgac   2340
tttgttcccg cagctgagct gaaggatcag aacgaaatca ctgttgtact gggctaa      2397
```

<210> SEQ ID NO 6
<211> LENGTH: 798
<212> TYPE: PRT
<213> ORGANISM: Ruminococcus champanellensis
<220> FEATURE:
<221> NAME/KEY: MISC_FEATURE
<222> LOCATION: (1)..(798)
<223> OTHER INFORMATION: RchCdp1_wild type protein

<400> SEQUENCE: 6

```
Met Gln Tyr Gly Tyr Phe Asp Leu Ala Asn Lys Glu Tyr Val Ile Thr
1               5                   10                  15

Arg Pro Asp Thr Pro Ala Pro Trp Ala Asn Tyr Leu Gly Asp Pro Glu
            20                  25                  30

Tyr Gly Ala Met Ile Ser Asn Ala Cys Gly Tyr Ser Phe Val Lys
                35                  40                  45

Ser Gly Ala Asn Gly Arg Ile Ser Arg Phe Arg Phe Asn Ser Asn Met
    50                  55                  60

Ala Leu Pro Gly Arg Tyr Ile Tyr Ile Arg Asp Asn Asp Thr Ala Asp
65                  70                  75                  80

Tyr Trp Ser Ala Ser Trp Gln Pro Val Gly Lys Pro Leu Asp Gln Tyr
                85                  90                  95

Lys Ser Val Cys Arg His Gly Thr Ala Tyr Thr Ile Met Thr Ala Asp
                100                 105                 110

Tyr Ala Ser Val His Ser Glu Thr Thr Tyr Tyr Val Pro Tyr His Gln
            115                 120                 125

Thr Tyr Glu Val Trp Arg Thr Lys Ile Thr Asn Thr Ser Asp Lys Pro
130                 135                 140

Arg Lys Leu Ser Val Phe Gly Phe Val Glu Phe Thr Asn Asp Asn Asn
145                 150                 155                 160

Tyr Glu Gln Asp Gln Val Asn Leu Gln Tyr Thr Leu Phe Ile Thr Arg
                165                 170                 175

Thr Ser Phe Glu Glu Asn Arg Ile Ile Gln His Ile Asn Glu Asn Ser
            180                 185                 190

Gly Lys Asp Ala Ser Gly Ser Asn His Lys Glu Arg Phe Phe Gly Met
        195                 200                 205

Val Gly Ala Pro Val Ser Gly Trp Asn Gly Asn Leu Asp Ser Phe Ile
210                 215                 220

Gly Pro Tyr Arg Thr Tyr Ser Asn Pro Ile Ala Val Glu Gln Gly Lys
225                 230                 235                 240

Cys Asp Gly Ser Met Asn Tyr Asn Ser Asn Ala Cys Gly Ala Leu Gln
                245                 250                 255

Ser Asp Leu Glu Leu Thr Pro Gly Glu Thr Ala Glu Leu Ile Tyr Ile
            260                 265                 270

Leu Gly Gln Arg Asn Ser Ala Glu Ala Thr Ile Leu Asp Thr Tyr
        275                 280                 285

Lys Thr Leu Gly Lys Val Asp Ala Glu Ile Ala Glu Leu Lys Asn Phe
290                 295                 300

Trp His Lys Glu Leu Ser Asn Phe Gln Val Asn Thr Pro Ser Pro Glu
305                 310                 315                 320

Phe Asn Asn Met Ile Asn Val Trp Asn Ala Tyr Gln Cys Phe Ile Thr
                325                 330                 335

Phe Ile Trp Ser Arg Ala Ala Ser Phe Val Tyr Cys Gly Leu Arg Asn
            340                 345                 350

Gly Tyr Gly Tyr Arg Asp Thr Val Gln Asp Ile Gln Gly Ile Ile His
        355                 360                 365

Leu Asp Pro Glu Met Ala Ala Asp Lys Ile Arg Phe Met Leu Ser Ala
370                 375                 380

Gln Val Asp Asn Gly Gly Leu Pro Leu Val Lys Phe Asn His Asn
385                 390                 395                 400

Ala Gly His Glu Asn Thr Pro Asp Asp Pro Glu Tyr Val Lys Glu Thr
                405                 410                 415
```

Gly His Pro Ser Tyr Arg Ala Asp Asp Ala Leu Trp Leu Phe Pro Thr
              420                 425                 430

Ile Val Lys Tyr Ile Gly Glu Ser Gly Asn Lys Ala Phe Leu Asp Glu
              435                 440                 445

Val Ile Val Tyr Ala Asn Gly Glu Ala Thr Val Tyr Asp His Leu
              450                 455                 460

Lys Asn Ala Ile Arg Phe Ser Met Glu Arg Leu Gly Ala His Asp Met
465                 470                 475                 480

Pro Ala Gly Leu His Ala Asp Trp Asn Asp Cys Leu Arg Met Gly Ala
                  485                 490                 495

Lys Gly Glu Ser Thr Phe Val Ala Phe Gln Leu Tyr Tyr Ala Met Arg
                  500                 505                 510

Val Ile Arg Asp Met Ala Gln Gln Arg Gly Asp Ser Asp Tyr Val Ala
              515                 520                 525

Tyr Ile Asp Asp Ile Gln Ala Lys Leu Gly Ala Ser Leu Glu Lys Cys
              530                 535                 540

Trp Asp Gly Asp Arg Phe Ile Arg Gly Ile Arg Glu Asp Gly Val Val
545                 550                 555                 560

Val Gly Ala Lys Lys Asp Pro Glu Ala Ser Met Trp Leu Asn Pro Gln
                  565                 570                 575

Ser Trp Ala Val Ile Ser Gly Phe Ala Ser Lys Asp Gln Ala Glu Gln
                  580                 585                 590

Ser Met Glu Ser Val His Arg Ile Leu Asn Thr Pro Tyr Gly Ile Lys
              595                 600                 605

Leu Leu Asp Pro Pro Tyr Arg Ala His Tyr Phe Asp Gly Ala Leu Met
              610                 615                 620

His Ile Phe Asn Pro Asp Thr Lys Glu Asn Gly Gly Ile Phe Ser Gln
625                 630                 635                 640

Ser Gln Gly Trp Ala Ile Leu Ala Glu Ser Leu Leu Gly His Gly Asn
                  645                 650                 655

Arg Ala Phe Glu Tyr Phe Met Glu Ser Ser Pro Ala Ala Met Asn Asp
                  660                 665                 670

Arg Ala Glu Ile Arg Val Met Glu Pro Tyr Val His Gly Gln Phe Thr
              675                 680                 685

Glu Ser Thr Ala Ser Pro Tyr Ala Gly Arg Ser His Val His Trp Leu
              690                 695                 700

Thr Gly Thr Ala Ser Thr Val Met Val Gly Cys Val Glu Gly Ile Cys
705                 710                 715                 720

Gly Met Arg Pro Asn Ala Asp Gly Leu Val Ile Ser Pro Ser Ile Pro
                  725                 730                 735

Ser Ser Trp Asp Gly Phe Thr Ile Glu Lys Asn Phe Arg Gly Lys His
                  740                 745                 750

Leu Ser Ile Arg Val Glu Asn Pro Ser His Val Gln Ser Gly Val Lys
              755                 760                 765

Ser Leu Thr Leu Asn Gly Lys Glu Leu Ser Gly Asp Phe Val Pro Ala
              770                 775                 780

Ala Glu Leu Lys Asp Gln Asn Glu Ile Thr Val Val Leu Gly
785                 790                 795

<210> SEQ ID NO 7
<211> LENGTH: 2421
<212> TYPE: DNA
<213> ORGANISM: Artificial sequence
<220> FEATURE:

<223> OTHER INFORMATION: RchCdp1 with added sequences

<400> SEQUENCE: 7

```
atgcagtatg gctattttga tctggccaac aaagaatatg ttatcacccg tccggataca      60
ccggcaccgt gggcaaatta tctggtgat ccggaatatg gtgcaatgat tagcaataat     120
gcatgcggct atagctttgt taaaagcggt gcaaatggtc gtattagccg ttttcgtttt     180
aatagcaata tggcactgcc tggtcgctat atctatattc gtgataatga taccgcagac     240
tattggagcg caagctggca gccggttggt aaaccgctgg atcagtataa aagcgtttgt     300
cgtcatggca ccgcatatac cattatgacc gcagattatg caagcgttca tagcgaaacc     360
acctattatg ttccgtatca tcagacctat gaagtgtggc gtaccaaaat taccaatacc     420
agcgataaac cgcgtaaact gagcgttttt ggttttgtgg aattcaccaa cgataacaac     480
tatgaacagg atcaggtgaa tctgcagtat accctgttta ttacccgtac cagctttgaa     540
gaaaaccgca ttattcagca catcaatgaa acagcggta aagatgcaag cggcagcaat     600
cataaagaac gcttttttgg tatggttggt gcaccggtta gcggttggaa tggtaatctg     660
gatagcttta ttggtccgta tcgtacctat agcaatccga ttgcagttga acagggtaaa     720
tgtgatggta gcatgaacta atatagtaat gcatgtggtg cactgcagag cgatctggaa     780
ctgacaccgg gtgaaaccgc agaactgatt tatatcctgg gtcagcgtaa tagcgcagaa     840
gcagcaacca ttctggatac ctataaaacc ctgggtaaag tggatgcaga aattgccgaa     900
ctgaaaaact tttggcacaa agaactgagc aactttcagg ttaatacccc gagtccggaa     960
tttaacaata tgattaatgt gtggaacgcc tatcagtgct tcatcacctt tatttggagc    1020
cgtgcagcaa gctttgttta ttgtggtctg cgtaatggtt atggctatcg tgataccgtt    1080
caggatattc agggtattat tcatctggat cctgaaatgg cagccgataa aattcgtttt    1140
atgctgagcg cacaggttga taatggtggt ggtctgccgc tggtgaaatt taaccataat    1200
gcaggtcatg aaaacacacc ggatgatcct gagtatgtta agaaaccgg tcatccgagc    1260
tatcgtgcag atgatgcact gtggctgttt ccgaccattg tgaaatatat cggtgaaagc    1320
ggtaacaaag cctttctgga tgaagttatt gtgtatgcaa atggcggtga agcaaccgtt    1380
tatgatcatc tgaaaaatgc cattcgcttt agcatggaac gtctgggtgc acatgatatg    1440
cctgcaggtc tgcatgccga ttggaatgat tgtctgcgta tgggtgcaaa aggtgaaagc    1500
acctttgttg catttcagct gtattatgcc atgcgtgtta ttcgcgatat ggcacagcag    1560
cgtggtgata gcgattatgt tgcatatatt gatgacatcc aggcaaaact gggtgcaagc    1620
ctggaaaaat gttgggatgg tgatcgtttt attcgcggta ttcgtgaaga tggtgttgtt    1680
gttggtgcaa aaaagatcc ggaagcaagc atgtggctga tccgcagag ctgggcagtt    1740
attagcggtt ttgcaagcaa agatcaggca gaacagagca tggaaagcgt gcatcgtatt    1800
ctgaataccc gtatggtat taaactgctg acccaccgt atcgtgcaca ttatttgat    1860
ggtgccctga tgcatatctt taacccggat accaaagaaa acgtggtat ttttagccag    1920
agccagggtt gggcaattct ggcagaaagc ctgctgggtc atggtaatcg tgcatttgaa    1980
tactttatgg aaagcagtcc ggcagccatg aatgatcgtg ccgaaattcg tgtgatggaa    2040
ccgtatgttc atggtcagtt taccgaaagc accgcaagcc cgtatgcagg tcgtagccat    2100
gttcattggc tgaccggtac agcaagcacc gttatggtgg ttgtgttga aggtatttgt    2160
ggtatgcgtc cgaatgcaga tggtctggtt attagcccga gcattccgag cagctgggat    2220
ggttttacca ttgaaaaaaa ctttcgcggt aaacatctga gcattcgtgt tgaaaatccg    2280
```

-continued

```
agtcatgttc agagcggtgt gaaaagcctg accctgaatg gtaaagaact gtcaggtgat    2340
tttgttccgg cagcggaact gaaagatcag aatgaaatta ccgttgtgct gggcctcgag    2400
caccaccacc accaccactg a                                              2421
```

<210> SEQ ID NO 8
<211> LENGTH: 806
<212> TYPE: PRT
<213> ORGANISM: Artificial sequence
<220> FEATURE:
<223> OTHER INFORMATION: RchCdp1 with added sequences_protein

<400> SEQUENCE: 8

```
Met Gln Tyr Gly Tyr Phe Asp Leu Ala Asn Lys Glu Tyr Val Ile Thr
1               5                   10                  15

Arg Pro Asp Thr Pro Ala Pro Trp Ala Asn Tyr Leu Gly Asp Pro Glu
            20                  25                  30

Tyr Gly Ala Met Ile Ser Asn Asn Ala Cys Gly Tyr Ser Phe Val Lys
        35                  40                  45

Ser Gly Ala Asn Gly Arg Ile Ser Arg Phe Arg Phe Asn Ser Asn Met
    50                  55                  60

Ala Leu Pro Gly Arg Tyr Ile Tyr Ile Arg Asp Asn Asp Thr Ala Asp
65                  70                  75                  80

Tyr Trp Ser Ala Ser Trp Gln Pro Val Gly Lys Pro Leu Asp Gln Tyr
                85                  90                  95

Lys Ser Val Cys Arg His Gly Thr Ala Tyr Thr Ile Met Thr Ala Asp
            100                 105                 110

Tyr Ala Ser Val His Ser Glu Thr Thr Tyr Tyr Val Pro Tyr His Gln
        115                 120                 125

Thr Tyr Glu Val Trp Arg Thr Lys Ile Thr Asn Thr Ser Asp Lys Pro
    130                 135                 140

Arg Lys Leu Ser Val Phe Gly Phe Val Glu Phe Thr Asn Asp Asn Asn
145                 150                 155                 160

Tyr Glu Gln Asp Gln Val Asn Leu Gln Tyr Thr Leu Phe Ile Thr Arg
                165                 170                 175

Thr Ser Phe Glu Glu Asn Arg Ile Ile Gln His Ile Asn Glu Asn Ser
            180                 185                 190

Gly Lys Asp Ala Ser Gly Ser Asn His Lys Glu Arg Phe Phe Gly Met
        195                 200                 205

Val Gly Ala Pro Val Ser Gly Trp Asn Gly Asn Leu Asp Ser Phe Ile
    210                 215                 220

Gly Pro Tyr Arg Thr Tyr Ser Asn Pro Ile Ala Val Glu Gln Gly Lys
225                 230                 235                 240

Cys Asp Gly Ser Met Asn Tyr Asn Ser Asn Ala Cys Gly Ala Leu Gln
                245                 250                 255

Ser Asp Leu Glu Leu Thr Pro Gly Glu Thr Ala Glu Leu Ile Tyr Ile
            260                 265                 270

Leu Gly Gln Arg Asn Ser Ala Glu Ala Ala Thr Ile Leu Asp Thr Tyr
        275                 280                 285

Lys Thr Leu Gly Lys Val Asp Ala Glu Ile Ala Glu Leu Lys Asn Phe
    290                 295                 300

Trp His Lys Glu Leu Ser Asn Phe Gln Val Asn Thr Pro Ser Pro Glu
305                 310                 315                 320

Phe Asn Asn Met Ile Asn Val Trp Asn Ala Tyr Gln Cys Phe Ile Thr
                325                 330                 335
```

```
Phe Ile Trp Ser Arg Ala Ala Ser Phe Val Tyr Cys Gly Leu Arg Asn
                340                 345                 350

Gly Tyr Gly Tyr Arg Asp Thr Val Gln Asp Ile Gln Gly Ile Ile His
            355                 360                 365

Leu Asp Pro Glu Met Ala Ala Asp Lys Ile Arg Phe Met Leu Ser Ala
        370                 375                 380

Gln Val Asp Asn Gly Gly Leu Pro Leu Val Lys Phe Asn His Asn
385                 390                 395                 400

Ala Gly His Glu Asn Thr Pro Asp Asp Pro Glu Tyr Val Lys Glu Thr
                405                 410                 415

Gly His Pro Ser Tyr Arg Ala Asp Ala Leu Trp Leu Phe Pro Thr
            420                 425                 430

Ile Val Lys Tyr Ile Gly Glu Ser Gly Asn Lys Ala Phe Leu Asp Glu
        435                 440                 445

Val Ile Val Tyr Ala Asn Gly Gly Glu Ala Thr Val Tyr Asp His Leu
    450                 455                 460

Lys Asn Ala Ile Arg Phe Ser Met Glu Arg Leu Gly Ala His Asp Met
465                 470                 475                 480

Pro Ala Gly Leu His Ala Asp Trp Asn Asp Cys Leu Arg Met Gly Ala
                485                 490                 495

Lys Gly Glu Ser Thr Phe Val Ala Phe Gln Leu Tyr Tyr Ala Met Arg
            500                 505                 510

Val Ile Arg Asp Met Ala Gln Gln Arg Gly Asp Ser Asp Tyr Val Ala
        515                 520                 525

Tyr Ile Asp Asp Ile Gln Ala Lys Leu Gly Ala Ser Leu Glu Lys Cys
    530                 535                 540

Trp Asp Gly Asp Arg Phe Ile Arg Gly Ile Arg Glu Asp Gly Val Val
545                 550                 555                 560

Val Gly Ala Lys Lys Asp Pro Glu Ala Ser Met Trp Leu Asn Pro Gln
                565                 570                 575

Ser Trp Ala Val Ile Ser Gly Phe Ala Ser Lys Asp Gln Ala Glu Gln
            580                 585                 590

Ser Met Glu Ser Val His Arg Ile Leu Asn Thr Pro Tyr Gly Ile Lys
        595                 600                 605

Leu Leu Asp Pro Pro Tyr Arg Ala His Tyr Phe Asp Gly Ala Leu Met
    610                 615                 620

His Ile Phe Asn Pro Asp Thr Lys Glu Asn Gly Gly Ile Phe Ser Gln
625                 630                 635                 640

Ser Gln Gly Trp Ala Ile Leu Ala Glu Ser Leu Leu Gly His Gly Asn
                645                 650                 655

Arg Ala Phe Glu Tyr Phe Met Glu Ser Ser Pro Ala Ala Met Asn Asp
            660                 665                 670

Arg Ala Glu Ile Arg Val Met Glu Pro Tyr Val His Gly Gln Phe Thr
        675                 680                 685

Glu Ser Thr Ala Ser Pro Tyr Ala Gly Arg Ser His Val His Trp Leu
    690                 695                 700

Thr Gly Thr Ala Ser Thr Val Met Val Gly Cys Val Glu Gly Ile Cys
705                 710                 715                 720

Gly Met Arg Pro Asn Ala Asp Gly Leu Val Ile Ser Pro Ser Ile Pro
                725                 730                 735

Ser Ser Trp Asp Gly Phe Thr Ile Glu Lys Asn Phe Arg Gly Lys His
            740                 745                 750
```

```
Leu Ser Ile Arg Val Glu Asn Pro Ser His Val Gln Ser Gly Val Lys
        755             760             765
Ser Leu Thr Leu Asn Gly Lys Glu Leu Ser Gly Asp Phe Val Pro Ala
    770             775             780
Ala Glu Leu Lys Asp Gln Asn Glu Ile Thr Val Val Leu Gly Leu Glu
785             790             795             800
His His His His His His
            805
```